US010905832B2

(12) United States Patent
Takemoto

(10) Patent No.: US 10,905,832 B2
(45) Date of Patent: Feb. 2, 2021

(54) PROTECTIVE DEVICE AND MEDICAL INSTRUMENT ASSEMBLY

(71) Applicant: TERUMO KABUSHIKI KAISHA, Tokyo (JP)

(72) Inventor: Masafumi Takemoto, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 29 days.

(21) Appl. No.: 16/136,504

(22) Filed: Sep. 20, 2018

(65) Prior Publication Data

US 2019/0015599 A1   Jan. 17, 2019

Related U.S. Application Data

(63) Continuation of application No. PCT/JP2017/011945, filed on Mar. 24, 2017.

(30) Foreign Application Priority Data

Mar. 25, 2016  (JP) .................................. 2016-061231
Mar. 25, 2016  (JP) .................................. 2016-061251

(51) Int. Cl.
*A61M 5/32* (2006.01)
*A61M 5/46* (2006.01)

(52) U.S. Cl.
CPC .......... *A61M 5/326* (2013.01); *A61M 5/3245* (2013.01); *A61M 5/3271* (2013.01);
(Continued)

(58) Field of Classification Search
CPC .. A61M 5/326; A61M 5/3245; A61M 5/3271; A61M 5/3202; A61M 5/3269;
(Continued)

(56) References Cited

U.S. PATENT DOCUMENTS 6,379,337 B1   4/2002  Mohammad M. B. B. S.
2005/0096598 A1*  5/2005  Crawford .............. A61M 5/326
604/198

(Continued)

FOREIGN PATENT DOCUMENTS

JP   2002-532203 A   10/2002
JP   4981030 B2   7/2012
(Continued)

OTHER PUBLICATIONS

International Search Report and Written Opinion in PCT/JP2017/011945, dated Jun. 13, 2017, 12 pages.

(Continued)

*Primary Examiner* — Amber R Stiles
(74) *Attorney, Agent, or Firm* — Foley & Lardner LLP

(57) ABSTRACT

A protective device, for covering a needle tip of a needle of a medical instrument after puncturing of a puncture object by the needle, includes an inner cylinder, an outer cylinder, and a spring. The outer cylinder receives a cam structure of the inner cylinder and has a guide passage structure that includes one or more guide passages. The outer cylinder is provided with a lateral top part and a distal-end inclined edge part as resistance force generating parts for causing the inner cylinder to generate a resistance force at a puncture position or in the vicinity of the puncture position.

22 Claims, 16 Drawing Sheets

(52) U.S. Cl.
CPC ......... *A61M 5/3202* (2013.01); *A61M 5/3269* (2013.01); *A61M 5/46* (2013.01); *A61M 2005/3267* (2013.01)

(58) Field of Classification Search
CPC ............ A61M 5/46; A61M 2005/3267; A61M 5/3272
See application file for complete search history.

(56) References Cited

U.S. PATENT DOCUMENTS

| | | |
|---|---|---|
| 2005/0228345 A1 | 10/2005 | Yang et al. |
| 2007/0106225 A1* | 5/2007 | Millerd ............... A61M 5/3204 604/198 |
| 2007/0129674 A1* | 6/2007 | Liversidge ............ A61M 5/326 604/110 |
| 2009/0024093 A1 | 1/2009 | Carrel et al. |
| 2011/0160675 A1 | 6/2011 | Ruan et al. |
| 2011/0319832 A1 | 12/2011 | Chun |
| 2015/0190586 A1 | 7/2015 | Takemoto |
| 2018/0015233 A1 | 1/2018 | Takemoto |

FOREIGN PATENT DOCUMENTS

| | | |
|---|---|---|
| WO | WO-00/37125 A1 | 6/2000 |
| WO | WO-2013/134465 A1 | 9/2013 |
| WO | WO-2015/022787 A1 | 2/2015 |
| WO | WO-2016/121932 A1 | 8/2016 |

OTHER PUBLICATIONS

Office Action dated May 26, 2020 in corresponding Japanese Patent Application No. 2018-507433.
Extended European Search Report dated Nov. 16, 2019 in corresponding European Patent Application No. 17770396.4.

* cited by examiner

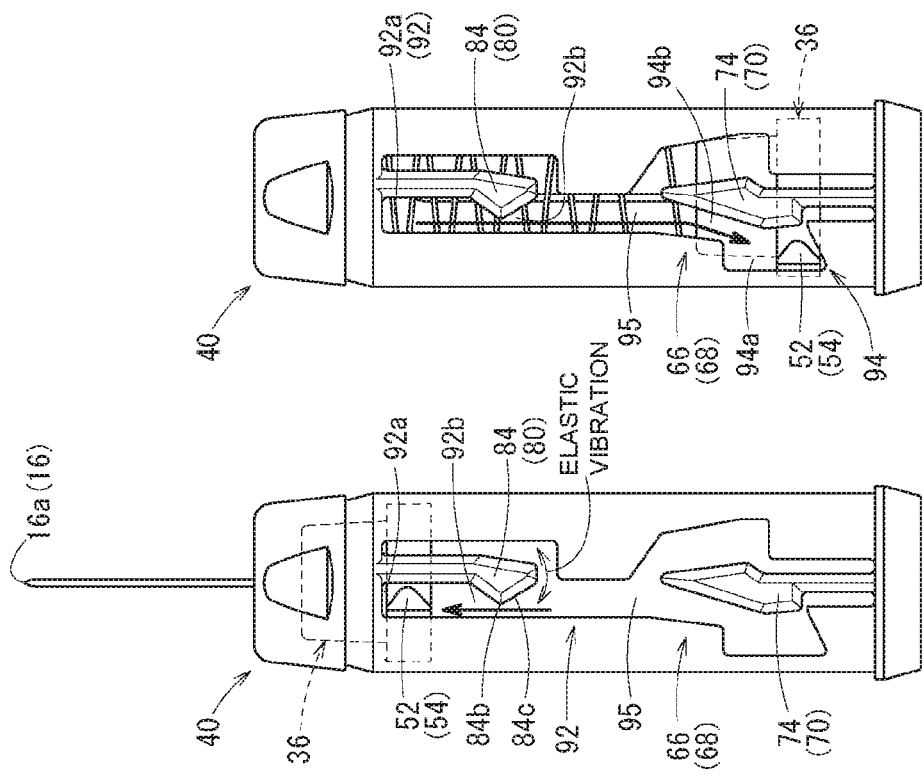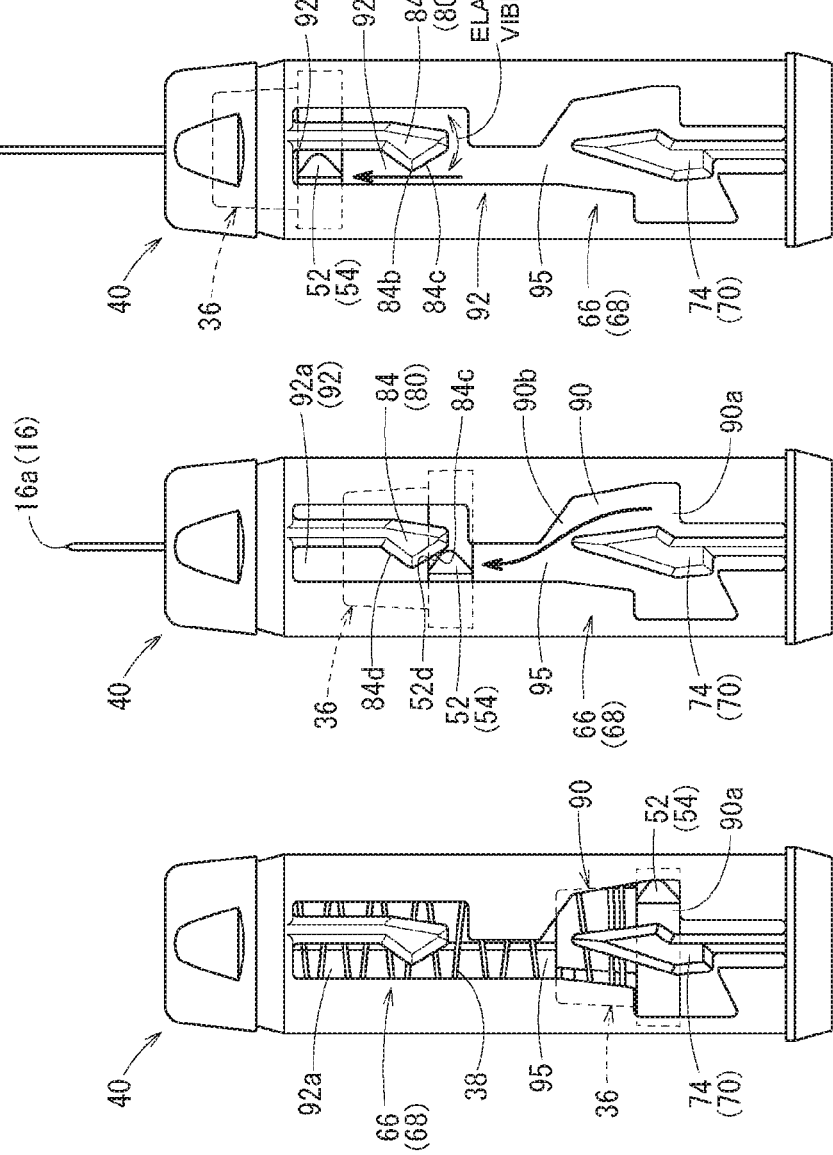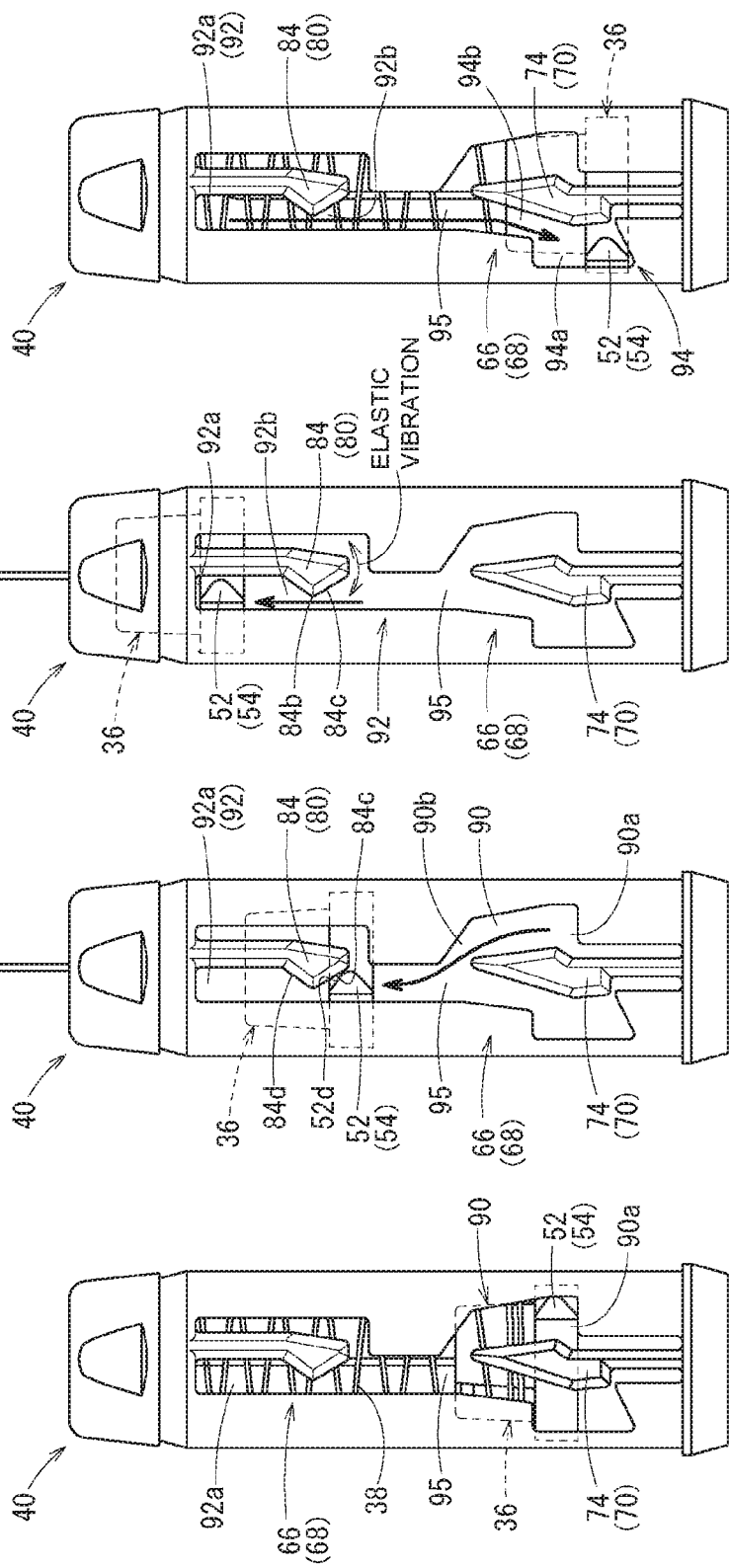

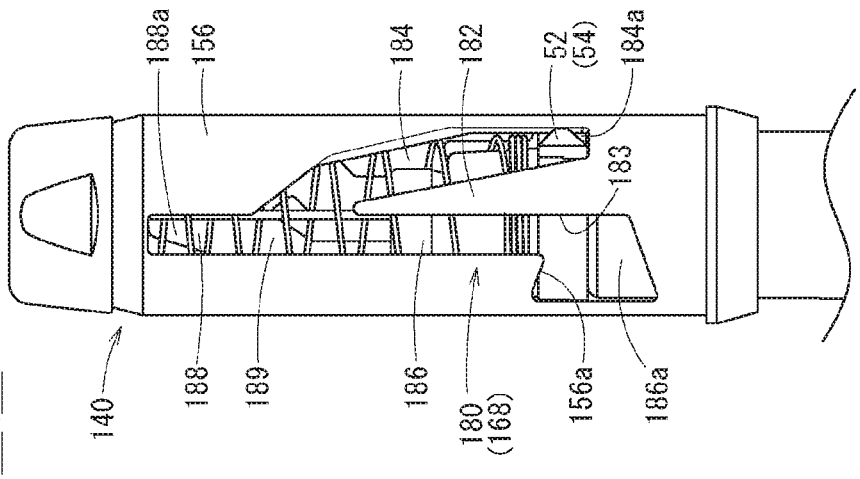
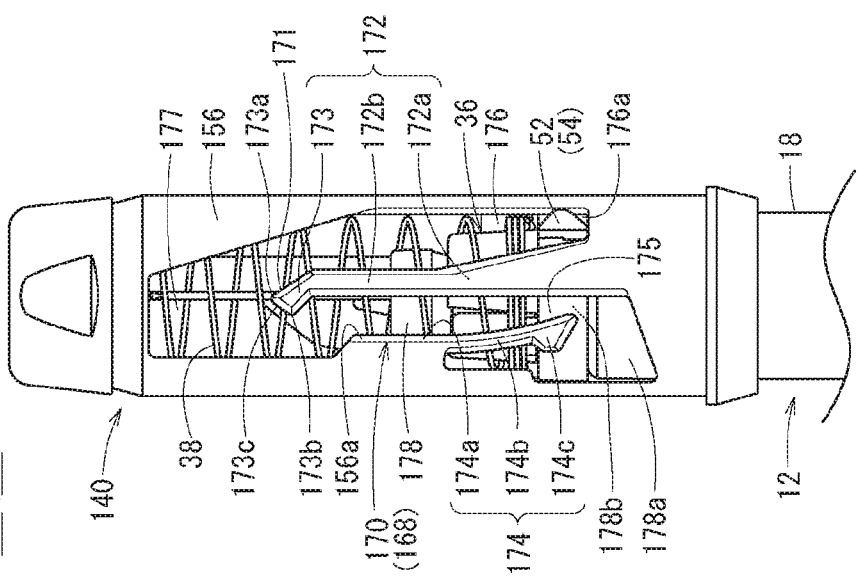

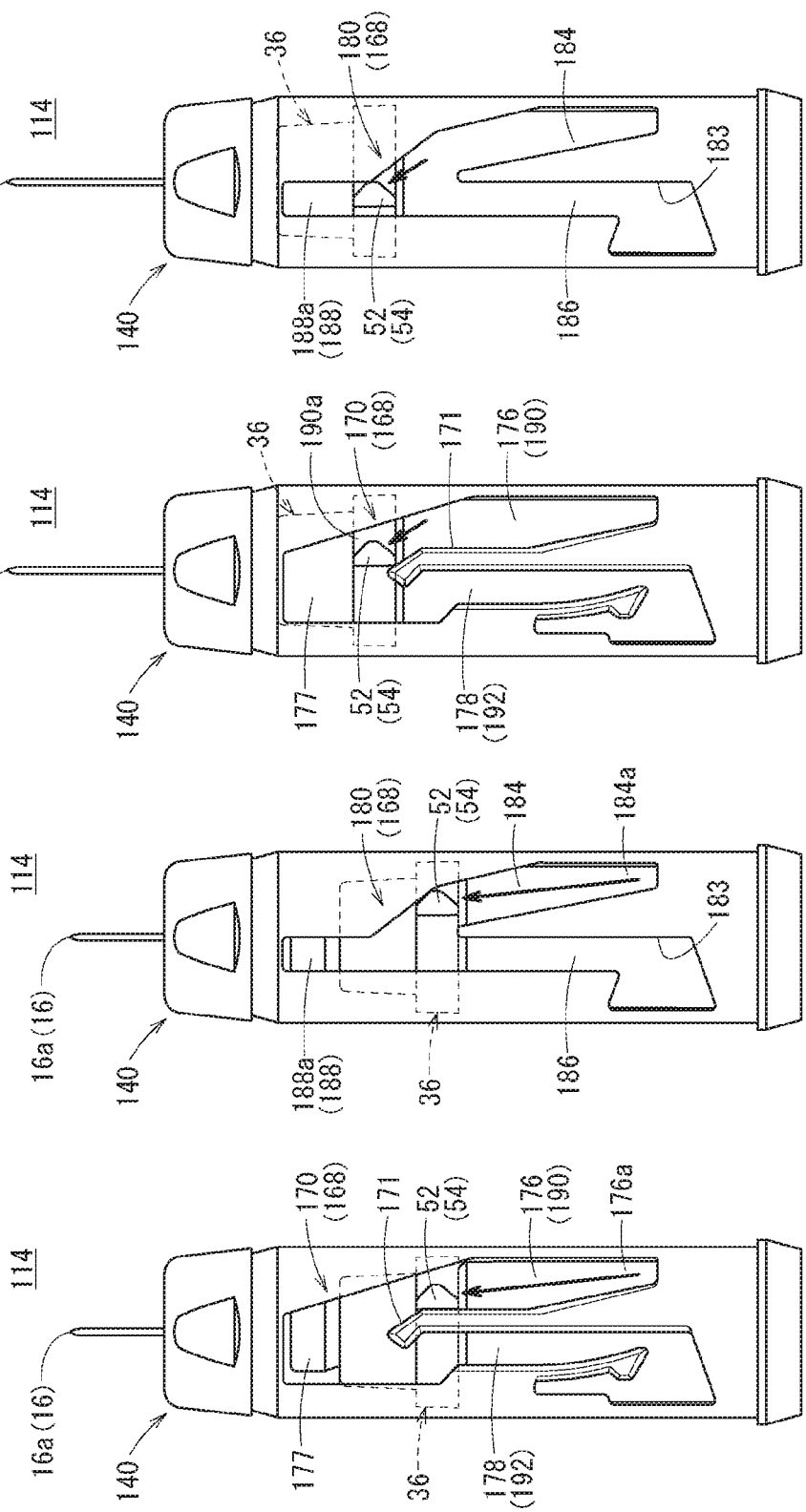

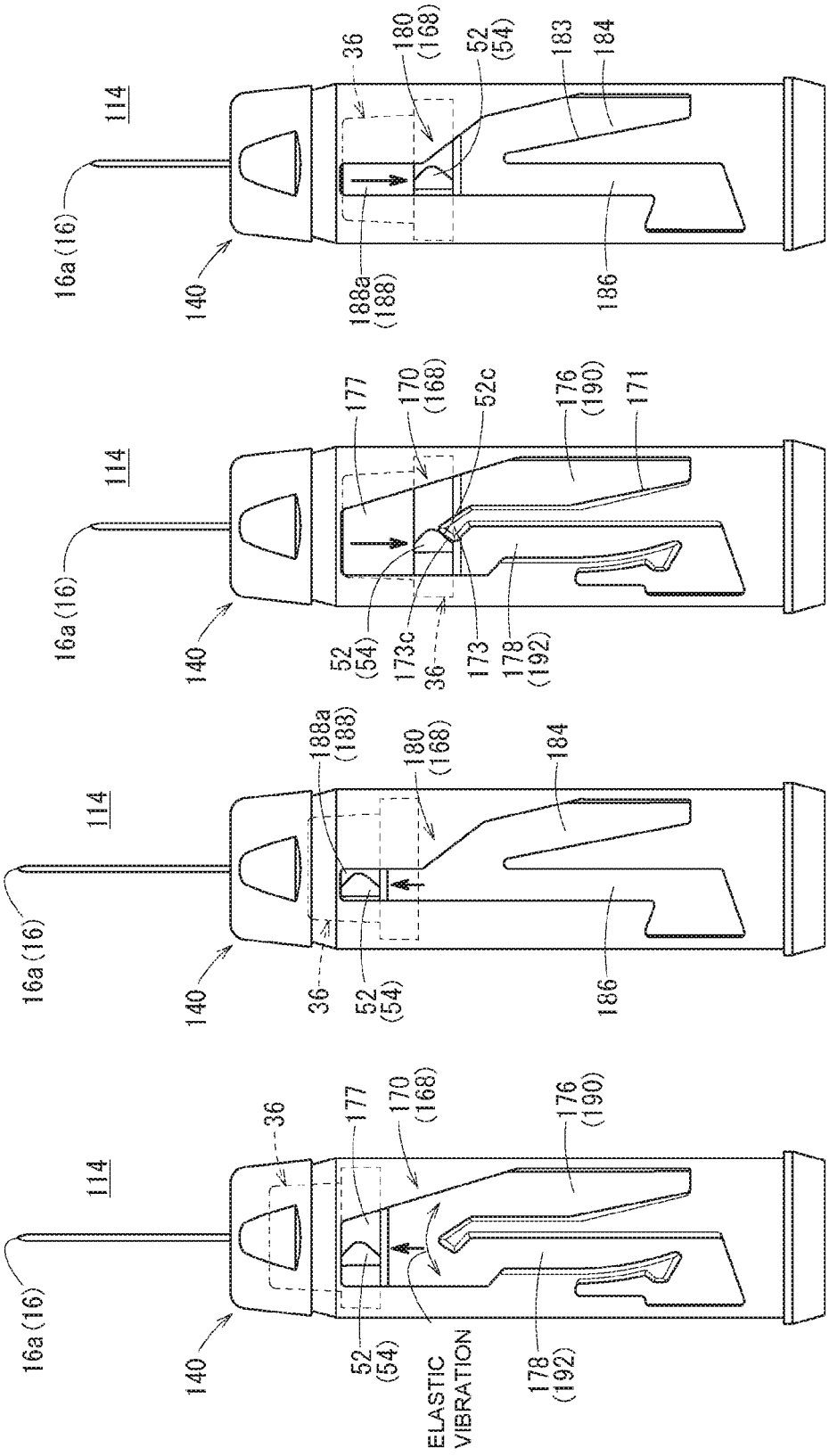

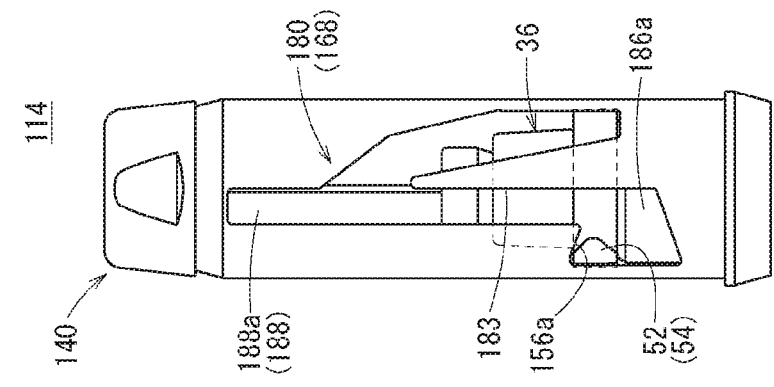
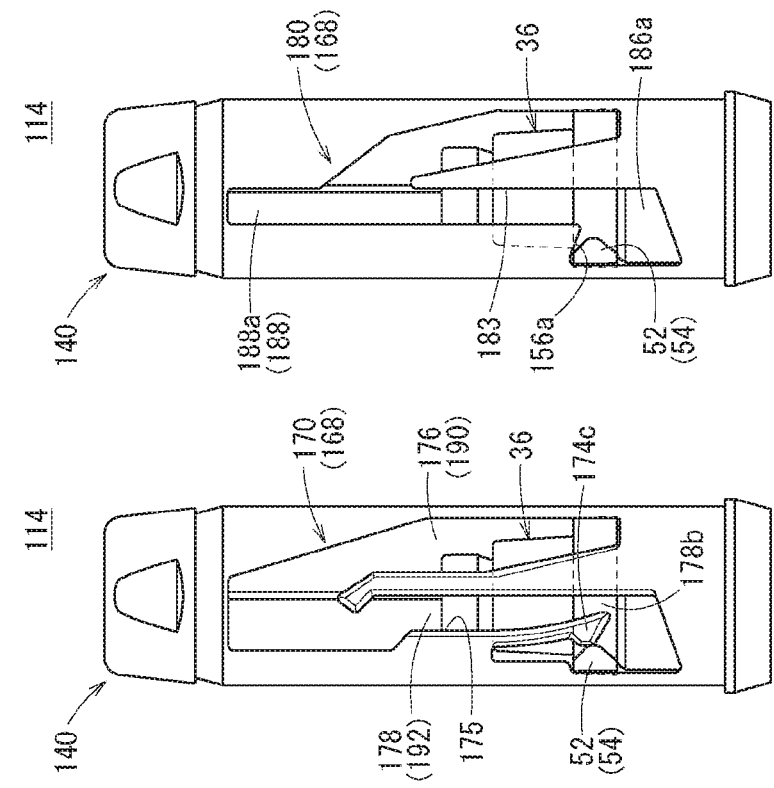
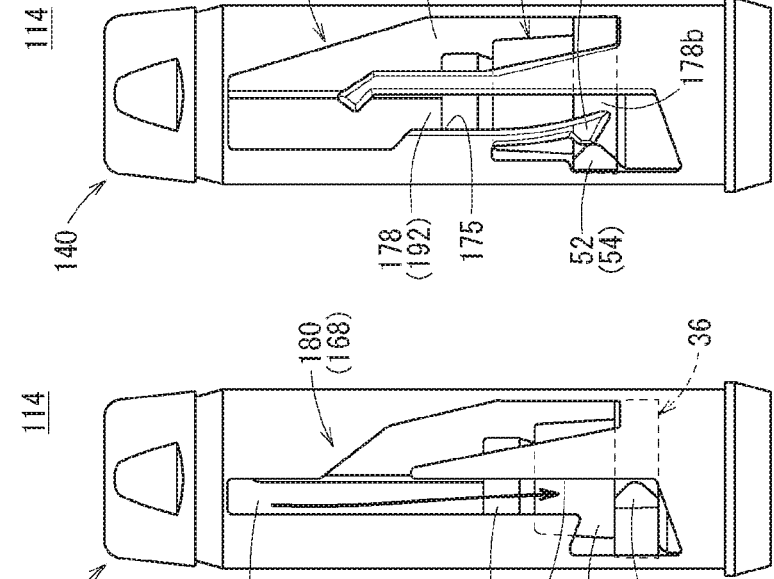
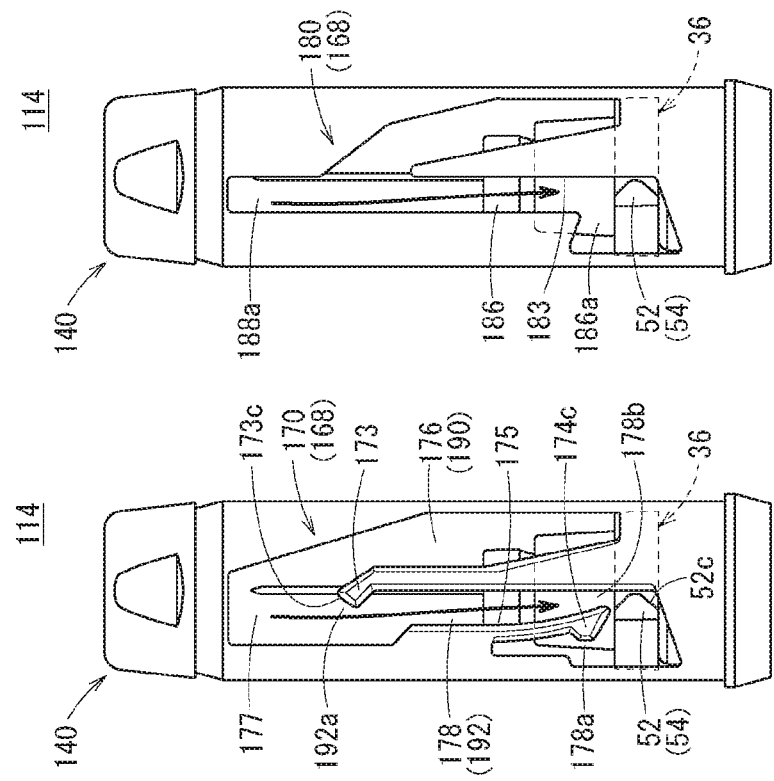

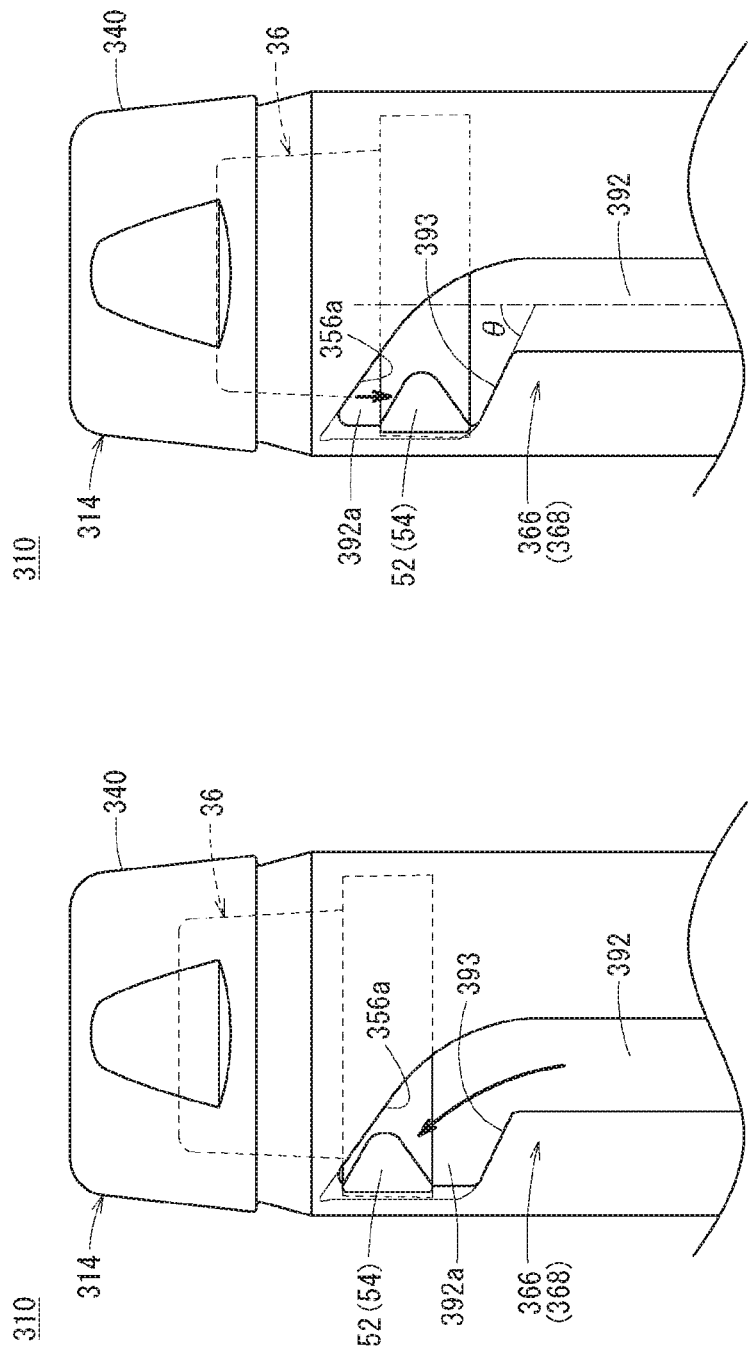

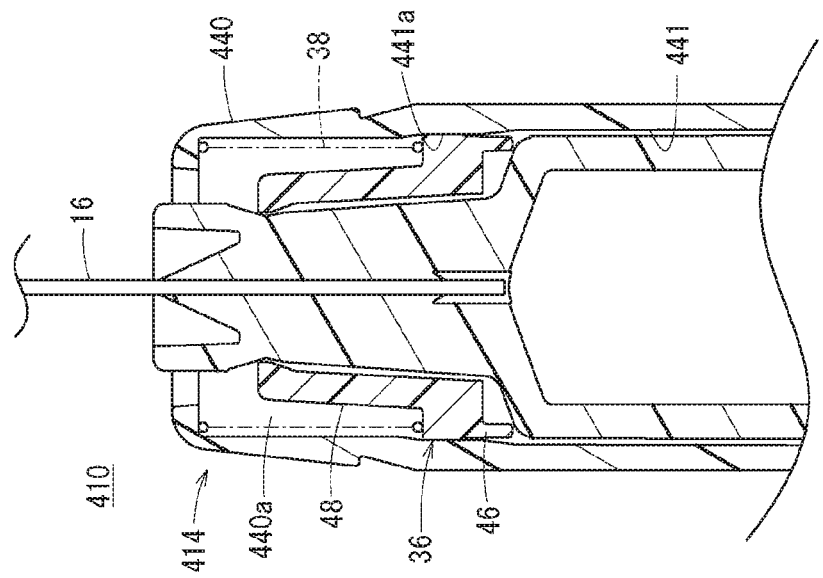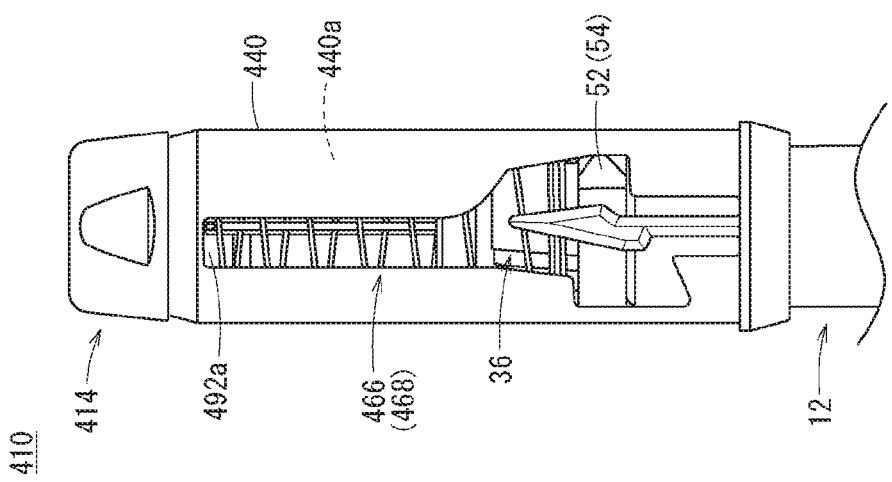

PROTECTIVE DEVICE AND MEDICAL INSTRUMENT ASSEMBLY

CROSS-REFERENCE TO RELATED APPLICATIONS

The present application is a bypass continuation of PCT Appl. No. PCT Application No. PCT/JP2017/011945, filed on Mar. 24, 2017, which claims priority to Japanese Appl. No. 2016-061231, filed on Mar. 25, 2016, and Japanese Appl. No. 2016-061251, filed on Mar. 25, 2016. The contents of these references are hereby incorporated by reference in their entireties.

BACKGROUND

The present disclosure relates to a protective device that covers a needle tip after puncturing a puncture target with a needle, and a medical instrument assembly to which the protective device is attached.

There is a syringe (medical instrument) in development that is used for injection and including a protective device (medical instrument assembly) to prevent inadvertent mispuncture with a needle after puncture.

For example, the protective device disclosed in JP 4981030 B2 includes a support having a needle and a sleeve movable relative to the support outside the support. The support includes a flexible tab extending in a distal direction and having a peg at its distal end. The sleeve has a U-shaped travel passage for receiving a peg of the support.

With puncture operation on the needle by the user, the protective device causes the support to advance with respect to the sleeve so as to expose the needle from the distal end. At this time, the peg is displaced to a puncture position on the distal side along the travel passage. After puncture, the sleeve is pushed out in a distal direction by a spring in the sleeve to displace the peg in a proximal direction on the travel passage, allowing the peg to be disposed at a final position on the proximal side with restricted re-movement in the distal direction. This operation allows the needle to be automatically covered by the sleeve so as to prohibit exposure.

SUMMARY

In JP 4981030 B2, the protective device contracts the spring to expose the needle from an outer cylinder (sleeve), with a biasing force of the spring in an exposed state being applied between the outer cylinder and an inner member (support). This allows the inner member and the syringe itself to easily move relative to the outer cylinder in the proximal direction. In particular, when the user performs depressing operation of a plunger of the syringe in order to administer the medicinal solution, force accompanying the depressing operation of the plunger is applied in a direction of releasing the syringe from the patient's skin. Accordingly, the force for pushing the syringe toward the patient's skin tends to be decreased, and the inner member biased by the spring might be instantaneously retracted with respect to the outer cylinder to release the needle from the patient.

Furthermore, because the outer cylinder (sleeve) thicker than the syringe is attached to the distal end portion of the syringe in the medical instrument assembly with the protective device, the user cannot easily view the needle exposed from the outer cylinder in the puncture with a needle, making it difficult to judge whether the puncture with the needle is being performed as intended. Furthermore, according to the protective device disclosed in JP 4981030 B2, a projection (peg) is positioned at a rotational position that is the same as an initial position in a standby state before puncture at a stage when the needle is sufficiently exposed and the projection (peg) is displaced to the distal side of a guide path (travel passage). In this case, a force in the proximal direction is applied to the projection when the user separates the syringe from the patient's skin and the outer cylinder advances, making it possible to allow the projection to return to the initial position, leading to inconvenience of disabling suppression of exposure of the needle.

Embodiments described in this disclosure have been developed in view of the above circumstances, and a first object of certain embodiments is to provide a protective device and a medical instrument assembly capable of suppressing unintended disengagement of a needle from a puncture target by reducing a retraction force of the inner member with respect to the outer cylinder in the exposed state of the needle, and capable of further enhancing handleability.

Moreover, a second object of certain embodiments is to provide a protective device and a medical instrument assembly capable of further enhancing the handleability of the protective device by favorably guiding the projection along the guide path and allowing the exposure of the needle from the outer cylinder to be sensed by the user.

In one embodiment, a protective device is configured to be attached to a medical instrument that includes a needle including a needle tip at distal end thereof; and a needle holding portion for holding the needle, the protective device being configured to cover the needle tip after puncturing a puncture target with the needle. The protective device includes: an inner member rotatably arranged in a circumferential direction with respect to the medical instrument and including a cam structure configured with one or more projections protruding outward in a radial direction; an outer cylinder that covers at least a portion of the needle and an outside of the inner member before puncture; and a biasing member that biases the outer cylinder in a distal direction with respect to the inner member, in which the outer cylinder includes a guide path structure configured with one or more guide paths that receive the cam structure and configured to rotate the inner member in accordance with a relative movement of the outer cylinder, and moves in a proximal direction relative to the inner member at the time of puncture to expose the needle tip and moves in a distal direction relative to the inner member by a biasing force of the biasing member after the puncturing to cover the needle tip, the guide path structure includes: an initial position where the cam structure is disposed before puncture, a puncture position being a position distal of the initial position, rotationally offset in a circumferential direction from the initial position and to which the cam structure moves at the time of puncture, a final position being a position proximal of the puncture position and to which the cam structure moves after the puncture, a distal direction passage that guides the cam structure from the initial position to the puncture position at the time of puncture; and a proximal direction passage that guides the cam structure from the puncture position to the final position after puncture, the outer cylinder includes a resistance force generator that generates, to the inner member, a resistance force against the relative movement of the inner member in the proximal direction with respect to the outer cylinder when the cam structure is positioned at the puncture position or in the vicinity of the puncture position, and the resistance force is smaller than the biasing force of the biasing member when the cam structure is positioned at the puncture position.

According to the above, with the resistance force generator that generates, to the inner member, a resistance force against the relative movement of the inner member in the proximal direction with respect to the outer cylinder when the cam structure is positioned at the puncture position or in the vicinity of the puncture position, the protective device is capable of reducing a retraction force of the inner member with respect to the outer cylinder in a state where the needle is exposed. For example, the retraction force of the inner member with respect to the outer cylinder is suppressed by the resistance force even when a force of a user pressing the medical instrument against the puncture target is decreased with the pushing operation of the plunger at the time of administration of the medicinal solution, making it possible to suppress inadvertent retraction of the inner member with respect to the outer cylinder, leading to satisfactory suppression of the disengagement of the needle from the puncture target. Furthermore, with the cam structure guided to the puncture position that is rotationally offset in the circumferential direction from the initial position, it is possible to avoid an inconvenience that the cam structure returns to the initial position and can be re-exposed when the cam structure guided to the puncture position retracts in the proximal direction. This enables the protective device to further enhance handleability. In addition, the resistance force of the resistance force generator is set to be smaller than the biasing force of the biasing member in a state where the cam structure is located at the puncture position. Therefore, the cam structure can reliably move to the final position through the resistance force generator after the puncture due to the biasing force of the biasing member.

In one aspect, the guide path structure includes a proximal direction passage elastically deformable portion that forms a proximal direction passage narrow portion in a middle of the proximal direction passage together with an edge portion of the proximal direction passage, the proximal direction passage narrow portion including a width smaller than a width of the projection in the proximal direction passage, in a middle of the proximal direction passage, and that elastically deforms so as to widen the width of the proximal direction passage narrow portion in accordance with contact with the projection such that the cam structure is allowed to move from the puncture position to the final position, and such that the cam structure is restricted from moving from the final position to the proximal direction passage by contact with the projection, the distal direction passage includes an inclined passage diagonally extending in the distal direction, and the proximal direction passage linearly extends along an axial direction of the outer cylinder at least from a vicinity of the proximal end of the puncture position to the proximal direction passage elastically deformable portion.

With this configuration, there is substantially no portion, other than the resistance force generator, that reduces the retraction force of the inner member with respect to the outer cylinder between the vicinity of the proximal end of the puncture position and the proximal direction passage narrow portion, making it possible to allow the projection to easily pass through the proximal direction passage narrow portion while elastically deforming the proximal direction passage elastically deformable portion on the basis of the biasing force of the biasing member. Therefore, the cam structure guided to the puncture position can be further reliably moved to the final position.

In one aspect, the guide path has the resistance force generator configured to come in contact with a side portion or a proximal end portion of the cam structure that has moved to the puncture position or to the vicinity of the puncture position.

With this configuration, resistance force can be easily generated in the cam structure that has moved to the puncture position.

In one aspect, the guide path includes an elastically deformable portion being elastically deformable, the elastically deformable portion includes: an elastically deformable main body connected to a peripheral wall of the outer cylinder; and a protruding portion protruding from the elastically deformable main body into the guide path, and that the protruding portion functions as the resistance force generator that generates the resistance force by the contact with the projection located at the puncture position or located in the vicinity of the puncture position.

This makes it easy to allow the cam structure to move in the proximal direction from the puncture position by the elastic deformation of the elastically deformable main body while generating the resistance force to the inner member by the contact between the protruding portion and the projection.

In one aspect, the protruding portion includes, on the distal side, a distal side inclined surface having a protruding amount into the guide path gradually increasing in the proximal direction.

This configuration makes it easier for the elastically deformable main body to elastically deform in the circumferential direction of the outer cylinder by the contact between the protruding portion and the projection.

In one aspect, the elastically deformable main body includes: a distal end portion connected to a peripheral wall of the outer cylinder; and a proximal end portion that is a free end, and the elastically deformable main body preferably extends from a distal end of the guide path in the proximal direction along the axial direction of the outer cylinder until passing over the puncture position, and the protruding portion is preferably disposed at the proximal end portion.

This makes it possible to reduce an extending length of the elastically deformable main body and increase the elastic force of the elastically deformable portion. Accordingly, this makes it possible to increase the resistance force generated in the cam structure and further reduce the retraction force of the inner member with respect to the outer cylinder.

In one aspect, the elastically deformable main body includes: a proximal end portion connected to the peripheral wall of the outer cylinder; and a distal end portion that is a free end, and the elastically deformable main body preferably extends from a proximal end of the guide path or from a middle of the distal direction passage in the distal direction along the axial direction of the outer cylinder until the vicinity of the proximal end of the puncture position, and the protruding portion may preferably be disposed at the distal end portion.

This makes it possible to increase the extending length of the elastically deformable main body and weaken the elastic force of the elastically deformable portion. Accordingly, this makes it possible to weaken the resistance force generated in the cam structure and more easily allow movement of the cam structure from the puncture position in the proximal direction.

In one aspect, the elastically deformable portion is disposed between the initial position and the puncture position in the circumferential direction of the outer cylinder, and functions as a distal direction passage elastically deformable portion to prevent the cam structure that has moved to the puncture position from moving to the initial position.

Thus, it is possible to move the cam structure more reliably from the puncture position to the final position.

In one aspect, the guide path includes a clamping portion including a width narrower than a width of the projection at the puncture position or in the vicinity of the proximal end of the puncture position, and the clamping portion may clamp the projection at an edge portion constituting the clamping portion to function as the resistance force generator that generates the resistance force.

With this configuration, it is possible to easily set the resistance force of the inner member. Furthermore, this can simplify the shape of the guide path and enhance the productivity of the device.

In one aspect, the guide path includes, in the vicinity of the proximal end of the puncture position, an inclined edge portion inclined at a predetermined angle with respect to the axial direction of the outer cylinder and constituting the guide path, and the inclined edge portion may preferably function as the resistance force generator that generates the resistance force by contact with the projection located at the puncture position or located in the vicinity of the puncture position.

This can simplify the shape of the guide path and increase the productivity of the device.

In one aspect, the outer cylinder has a contact inner surface that comes in contact with an outer surface of the inner member, and the contact inner surface may preferably function as the resistance force generator that generates the resistance force by the contact with the outer surface of the inner member when the projection is positioned at the puncture position or in the vicinity of the puncture position.

This can simplify the shape of the guide path and increase the productivity of the device, while enhancing the degree of freedom in designing the guide path structure.

In another embodiment, a protective device is configured to be attached to a medical instrument that includes a needle including a needle tip at distal end thereof; and a needle holding portion for holding the needle, the protective device being configured to cover the needle tip after puncturing a puncture target with the needle. The protective device includes: an inner member rotatably arranged in a circumferential direction on an outside of the medical instrument and including a cam structure configured with one or more projections protruding outward in a radial direction and; an outer cylinder that covers at least a portion of the needle and an outside of the inner member before puncture; and a biasing member that biases the outer cylinder in a distal direction with respect to the inner member, in which the outer cylinder includes a guide path structure configured with one or more guide paths that receives the cam structure and configured to rotate the inner member in accordance with a relative movement of the outer cylinder, and moves in a proximal direction relative to the inner member at the time of puncture to expose the needle tip and moves in a distal direction relative to the inner member by a biasing force of the biasing member after the puncturing to cover the needle tip, the guide path structure includes: an initial position where the cam structure is disposed before puncture, a puncture position being a position distal of the initial position, rotationally offset in a circumferential direction from the initial position and to which the cam structure moves at the time of puncture, a final position being a position proximal of the puncture position and to which the cam structure moves after the puncture, a distal direction passage that guides the cam structure from the initial position to the puncture position at the time of puncture; and a proximal direction passage that guides the cam structure from the puncture position to the final position after puncture, and the distal direction passage includes, in the vicinity of the proximal end of the puncture position, a click feeling generator that generates a click feeling with passage of the cam structure.

According to the above, the protective device includes the click feeling generator that generates a click feeling with the passage of the cam structure, making it possible to allow the user to recognize that the needle is sufficiently exposed from the outer cylinder. In addition, because the click feeling generator is provided in the vicinity of the proximal end of the puncture position, the cam structure can be located at a puncture position that is rotationally offset from the initial position in the circumferential direction immediately after user senses the click feeling or simultaneously with the sensing. Therefore, it is possible to prevent the cam structure from returning from the puncture position to the initial position after the user senses a click feeling. That is, the protective device can guide the projection satisfactorily along the guide path while enabling the user to sense the exposure of the needle from the outer cylinder, making it possible to further improve the handleability of the protective device.

In one aspect, the click feeling generator is provided at a position that is rotationally offset from the initial position in the circumferential direction.

This makes it possible to reliably prevent the cam structure from returning to the initial position after the user senses a click feeling.

In one aspect, the click feeling generator is an elastically deformable portion that elastically deforms by a contact with the cam structure and that generates a click feeling by elastic return after passages of the cam structure.

This makes it possible to easily provide the click feeling generator in the guide path structure and simplify the device.

In one aspect, the elastically deformable portion includes: an elastically deformable main body connected to a peripheral wall of the outer cylinder; and a protruding portion protruding to an inside of the guide path from the elastically deformable main body, in which the elastically deformable main body preferably elastically deforms in the circumferential direction of the outer cylinder with the contact between the protruding portion and the cam structure.

This makes it possible to reliably allow the elastically deformable main body to elastically deform in the circumferential direction of the outer cylinder by the contact between the protruding portion and the cam structure, and to generate a reliable click feeling at the time of elastic return of the elastically deformable main body.

In one aspect, the protruding portion includes a proximal side inclined surface having a protruding amount into the guide path gradually increasing in the distal direction.

This configuration makes it easier for the elastically deformable main body to elastically deform in the circumferential direction of the outer cylinder by the contact between the protruding portion and the cam structure.

In one aspect, an outer circumferential surface of the outer cylinder includes a cover to cover the guide path structure.

Because the position of the cam structure cannot be easily recognized in the configuration of covering the outer circumferential surface of the outer cylinder with the cover, making it further difficult to recognize an exposure state of the needle. To manage this, with a click feeling generated with the movement of the cam structure, the click feeling generator can satisfactorily inform the user that the needle is sufficiently exposed.

In another embodiment, a medical instrument assembly includes the protective device and the medical instrument to which the protective device is attached.

In this manner, with the presence of the medical instrument assembly with the protective device attached to the medical device, the user can immediately use the medical instrument assembly, leading to further enhancement of the usability.

In one aspect, the medical instrument is a prefilled syringe including: a barrel portion formed on a proximal side of the needle holding portion; a liquid stored in the barrel portion; and a cap for sealing the needle tip, and being configured to discharge the liquid from the needle tip.

With the medical instrument configured as a prefilled syringe in this manner, the user can immediately use the medical instrument assembly having the protective device, omitting the work of filling the medical instrument with a liquid.

According to certain embodiments of the present disclosure, the protective device and the medical instrument assembly are capable of suppressing disengagement of a needle from a puncture target by reducing a retraction force of the inner member with respect to the outer cylinder in the exposed state of the needle, and capable of further enhancing handleability.

BRIEF DESCRIPTION OF THE DRAWINGS

FIG. 6A is a partial side view illustrating first operation of the medical instrument assembly at the time of puncture. FIG. 6B is a partial side view illustrating second operation of the medical instrument assembly following FIG. 6A. FIG. 6C is a partial side view illustrating third operation of the medical instrument assembly following FIG. 6B. FIG. 6D is a partial side view illustrating fifth operation following FIG. 7B.

FIG. 8A is a first side view illustrating a distal end portion of a medical instrument assembly to which a protective device according to a second embodiment is attached. FIG. 8B is a second side view illustrating an opposite side of the first side view of FIG. 8A.

FIG. 10A is a partial side view illustrating first operation on a first guide path side of the medical instrument assembly in FIG. 8A. FIG. 10B is a partial side view illustrating first operation on a second guide path side of the medical instrument assembly in a same manner. FIG. 10C is a partial side view illustrating second operation following FIG. 10A. FIG. 10D is a partial side view illustrating the second operation following FIG. 10B.

FIG. 11A is a partial side view illustrating third operation following FIG. 10C. FIG. 11B is a partial side view illustrating the third operation following FIG. 10D. FIG. 11C is a partial side view illustrating the fourth operation following FIG. 11A. FIG. 11D is a partial side view illustrating the fourth operation following FIG. 11B.

FIG. 12A is a partial side view illustrating fifth operation following FIG. 11C. FIG. 12B is a partial side view illustrating the fifth operation following FIG. 11D. FIG. 12C is a partial side view illustrating sixth operation following FIG. 12A. FIG. 12D is a partial side view illustrating the sixth operation following FIG. 12B.

FIG. 15A is a partial side view illustrating a state in which the projection has moved to a puncture position in the medical instrument assembly of FIG. 14. FIG. 15B is a partial side view illustrating a state in which the resistance force is generated in the medical instrument assembly of FIG. 14.

FIG. 16A is a partial side view illustrating a distal end portion of a medical instrument assembly to which a protective device according to a fifth embodiment is attached. FIG. 16B is an enlarged partial side view illustrating a state in which an inner cylinder of FIG. 16A has moved to the puncture position.

DETAILED DESCRIPTION

Hereinafter, embodiments (first to fifth embodiments) of a protective device and a medical instrument assembly according to the present disclosure will be described in detail with reference to the accompanying drawings.

First Embodiment

Figure 1:
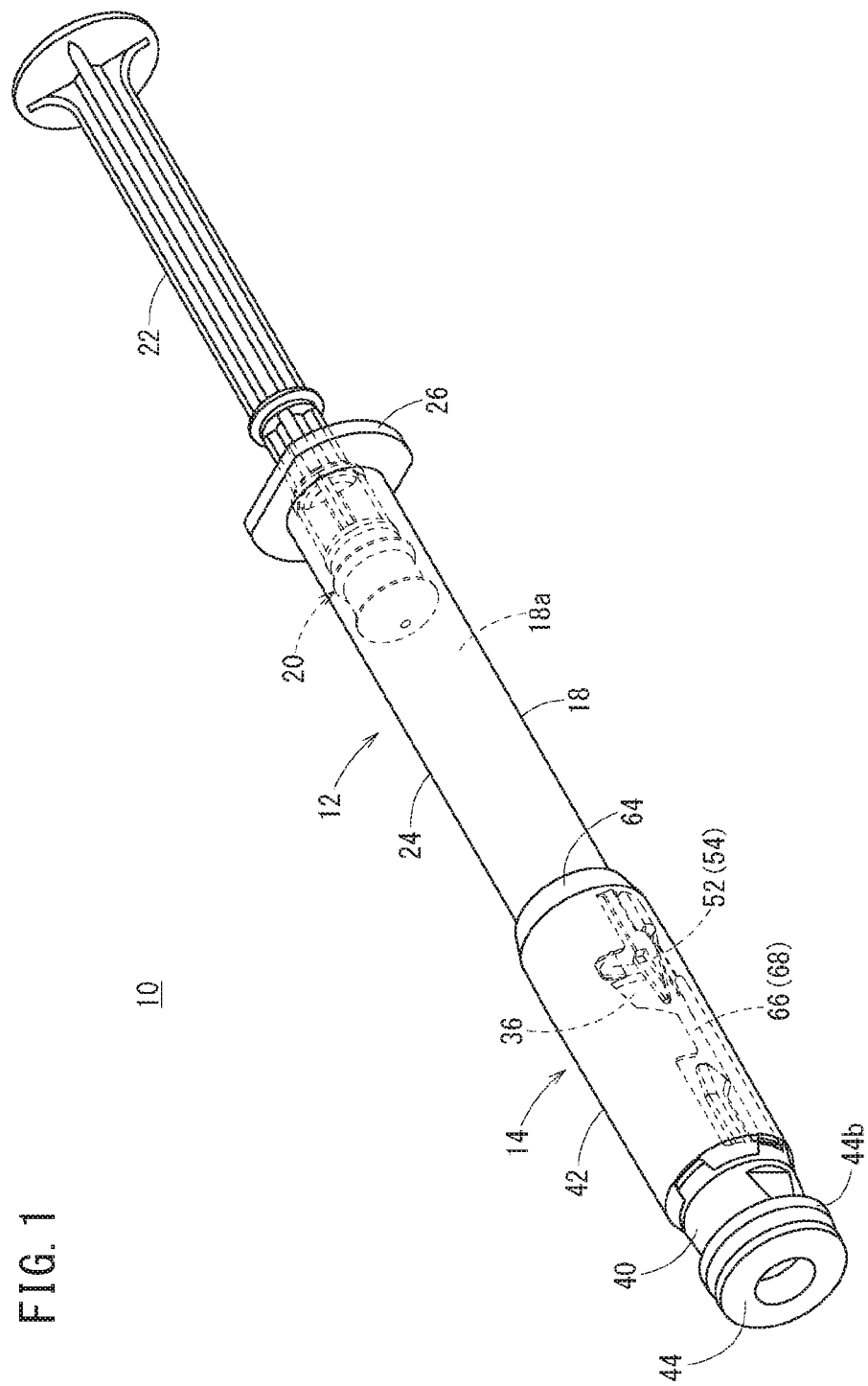
FIG. 1 is a perspective view illustrating an overall configuration of a medical instrument assembly to which a protective device according to a first embodiment is attached.

As illustrated in FIG. 1, a medical instrument assembly 10 according to a first embodiment has a configuration in which a protective device 14 is attached to a syringe 12 (medical instrument). Furthermore, the medical instrument assembly 10 is provided to a user (medical staff and a patient oneself) as a prefilled syringe preliminarily filled with a medicinal solution. Note that the syringe 12 may be configured to be filled up with a medicinal solution by the user from a vial or the like, and the protective device 14 may be provided separately from the syringe 12 and attached thereafter.

The protective device 14 improves safety and hygiene prior to use of the syringe 12 and prevents leakage of the medicinal solution. At the time of use, a needle 16 (refer to FIG. 2) of the syringe 12 is exposed from the distal end under the operation of the user to enable the needle 16 to be punctured into the patient as a puncture target. After administering the medicinal solution from the needle 16, the protective device 14 is pulled away from the patient so as to automatically re-store the exposed needle 16 to increase safety after puncture.

Figure 2:
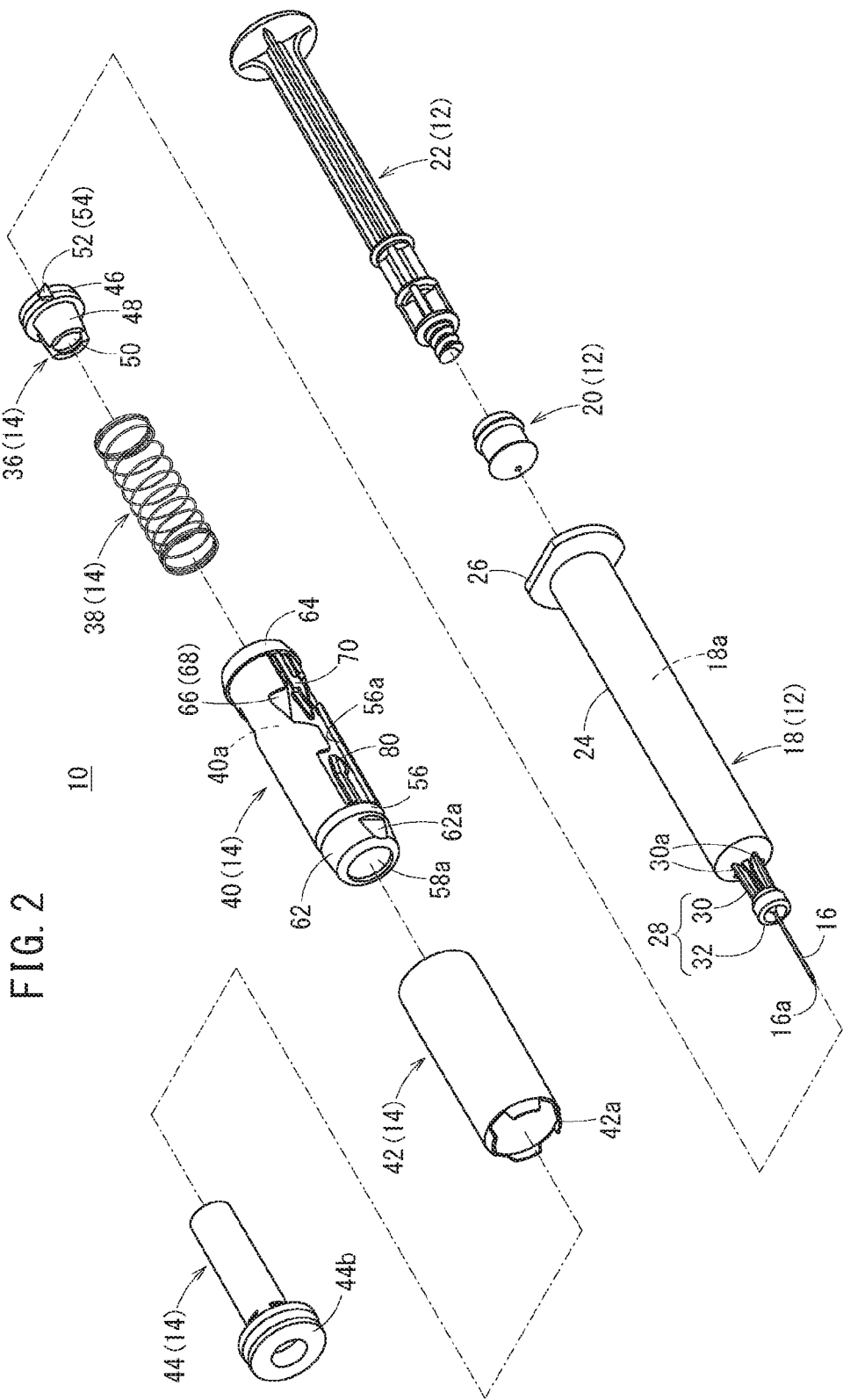
FIG. 2 is an exploded perspective view of the medical instrument assembly of FIG. 1.

As illustrated in FIG. 2, the syringe 12 to which the protective device 14 is assembled includes: a needle 16, a main body 18 having a storage space 18a to store a medicinal solution, a gasket 20 slidably inserted in the storage space 18a, and a plunger 22 for operating the gasket 20.

The needle 16 is appropriately formed in a small diameter, with a needle tip 16a at distal end thereof sharply formed. The needle 16 internally includes a lead-out path (not illustrated) for discharging the medicinal solution.

The main body 18 is formed by integrally molded portions, namely: a barrel portion 24 internally including the storage space 18a; a catch portion 26 provided on the proximal side of the barrel portion 24; and a needle holding portion 28 provided on the distal side of the barrel portion 24. The barrel portion 24 is formed in a cylindrical shape having a predetermined axial direction length and diameter in accordance with the amount of medicinal solution stored in the storage space 18a. The catch portion 26 is formed to protrude outward from an outer circumferential surface on the proximal side of the barrel portion 24 and configured to allow a jig for holding the main body 18 to be hooked when medicinal solution or the like is filled in the storage space 18a.

The needle holding portion 28 protrudes in the distal direction from the distal end of the barrel portion 24 having an axial center coaxial with an axial center of the barrel portion 24. It is preferable that the axial direction length of the needle holding portion 28 is formed to be shorter than the axial direction length of the portion of the needle 16 protruding toward the distal side from the needle holding portion 28. This allows for a reduction in the size of the medical instrument assembly 10. In order to hold the needle 16 with a short dimension, the needle holding portion 28 is configured with a support tube portion 30 on the proximal side and a bulging tube portion 32 on the distal side.

Figure 3:
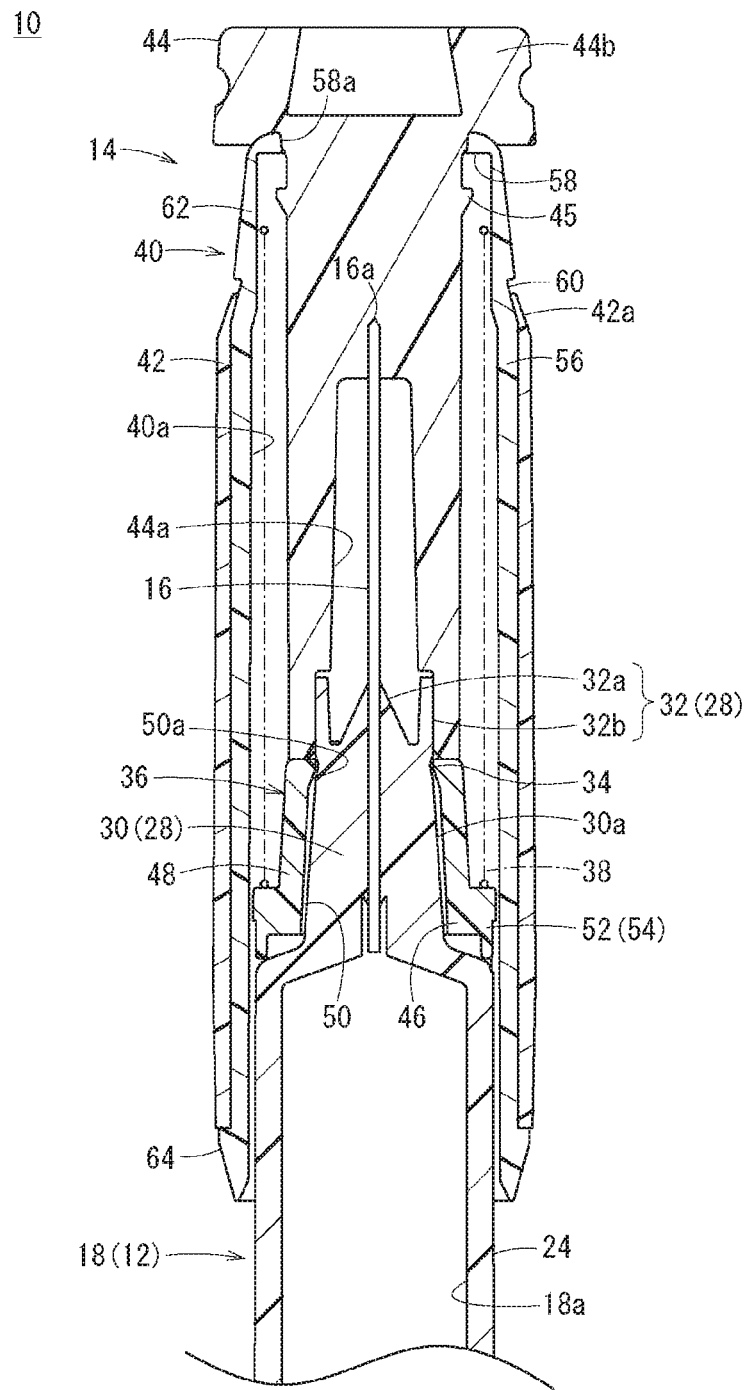
FIG. 3 is a side sectional view illustrating a distal end portion of the medical instrument assembly of FIG. 1.

The support tube portion 30 protrudes short from the main body 18 and fixes and holds the needle 16 at an axial center portion. Examples of methods of fixing the needle 16 include insert molding, thermal welding by radio frequency or laser, and bonding with an adhesive. A plurality of (four) reinforcement ribs 30a is (are) provided on the outer circumferential surface of the support tube portion 30 in order to increase the strength of the support tube portion 30. Each of the reinforcement ribs 30a extends from the main body 18 to the bulging tube portion 32. As illustrated in FIG. 3, a protruding height of each of the reinforcement ribs 30a gradually decreases in the distal direction, so as to be the lowest at a connecting portion of the bulging tube portion 32.

The bulging tube portion 32 has a central support portion 32a formed in a substantially conical shape for holding the needle 16 and an outer surrounding portion 32b surrounding one side of the central support portion 32a. The proximal side of the outer surrounding portion 32b is continuous with the reinforcement rib 30a, and the connection thereof tapers downward in the proximal direction to form a neck portion 34. The neck portion 34 has a function of enabling the inner cylinder 36 of the protective device 14 to be rotatably attached. The neck portion 34 is not limited to a tapered shape and may be formed simply as a step between the outer surrounding portion 32b and the reinforcement ribs 30a, for example.

Returning to FIG. 2, the plunger 22 of the syringe 12 serves as a pusher to be pressed by the user. The gasket 20 to be liquid-tightly inserted into the storage space 18a is attached to a distal end portion of the plunger 22. Note that the medical instrument assembly 10 can be configured to house the gasket 20 alone in the main body 18 before use without the plunger 22 attached.

Meanwhile, the protective device 14 is attached so as to cover the needle 16 and the distal side of the main body 18. As illustrated in FIGS. 2 and 3, the protective device 14 includes the inner cylinder 36 (inner member), a spring 38 (biasing member), an outer cylinder 40, and a cover 42. In addition, a cap 44 to cover the needle 16 of the syringe 12 is detachably attached to the protective device 14 before use.

Figure 4A:
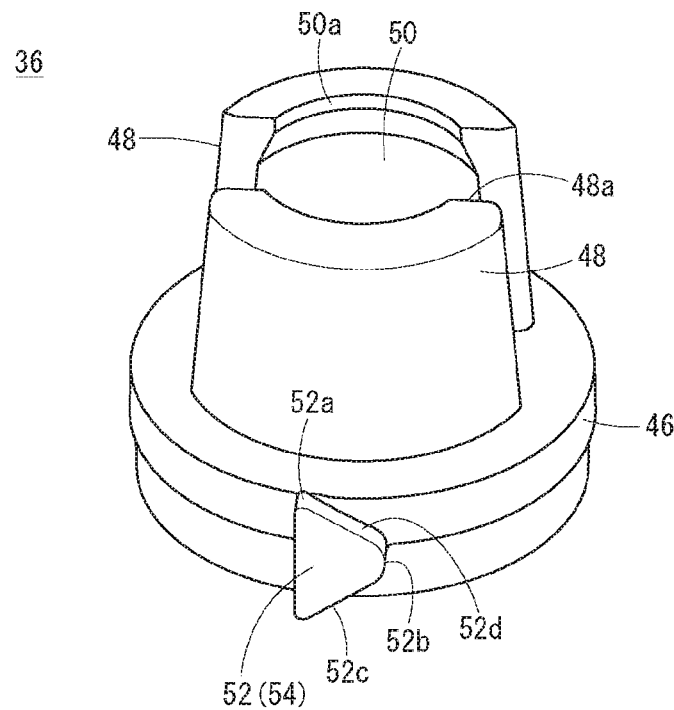
FIG. 4A is an enlarged perspective view of the inner cylinder of FIG. 1.
Figure 4B:
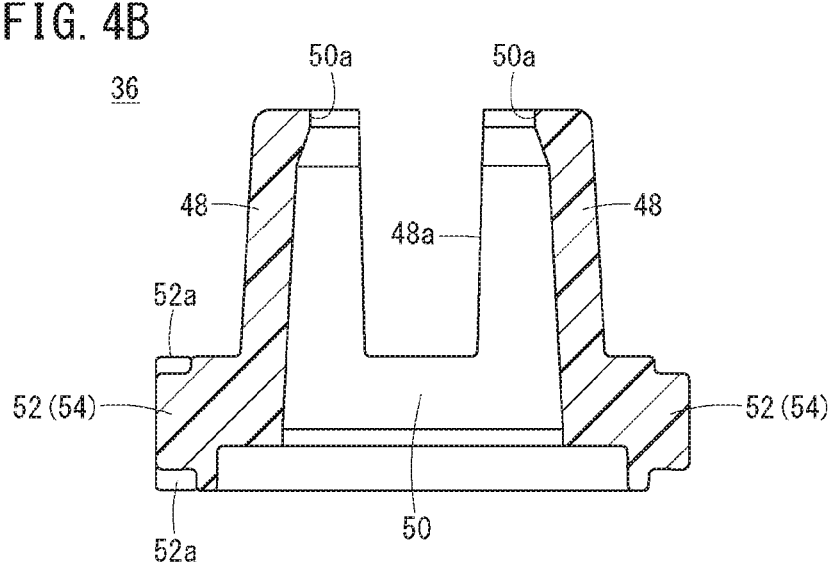
FIG. 4B is a side sectional view of the inner cylinder.

The inner cylinder 36 is rotatably attached around the needle holding portion 28 of the syringe 12. The inner cylinder 36 includes an annular portion 46 that surrounds the proximal side and a pair of protruding wall portions 48 connected to a distal end surface of the annular portion 46. As illustrated in FIGS. 4A and 4B, an attachment hole 50 for attachment to the needle holding portion 28 are provided inside the annular portion 46 and the pair of protruding wall portions 48.

The annular portion 46 is formed to have a relatively large thickness along the axial direction of the inner cylinder 36. The outer diameter of the annular portion 46 is set to substantially match the outer diameter of the barrel portion 24 in a state where the inner cylinder 36 is attached to the needle holding portion 28. On the outer circumferential surface of the annular portion 46, a pair of projections 52 is formed so as to protrude outward in the radial direction. A distal end surface of the annular portion 46 is a seat on which the proximal end of the spring 38 is disposed. Furthermore, the inner diameter of the attachment hole 50 of the annular portion 46 is formed to be slightly larger than the outer diameter of the support tube portion 30 (that is, the protruding height of the pair of reinforcement ribs 30a) in the attached state with the needle holding portion 28, thereby reducing frictional force due to contact with the support tube portion 30.

The protruding wall portion 48 protrudes from the inner side of the distal end surface of the annular portion 46 (closer to the attachment hole 50) and has an arc shape along a curvature of the annular portion 46 in plan view. The pair of protruding wall portions 48 faces each other, and a pair of split gaps 48a communicating with the attachment hole 50 is provided between the mutually arcuate end portions. When the inner cylinder 36 is attached to the needle holding portion 28, the pair of split gaps 48a allows the distal sides of the pair of protruding wall portions 48 to elastically separate from each other to facilitate attachment of the inner cylinder 36 to the needle holding portion 28.

The inner surface of the annular portion 46 and the pair of protruding wall portions 48 constituting the attachment hole 50 are formed in a tapered shape gradually narrowing in the distal direction in cross sectional view. A pair of hook portions 50a protruding slightly inward in the radial direction is provided on the inner surface of the distal side of the pair of protruding wall portions 48. The hook portion 50a is disposed in the neck portion 34 of the needle holding portion 28 in the attached state of the inner cylinder 36 and is caught by the distal end portion (outer surrounding portion 32b) of the neck portion 34. This prevents the inner cylinder 36 from coming out of the needle holding portion 28.

Meanwhile, the pair of projections 52 is integrally molded on the outer circumferential surface of the annular portion 46, and forms a cam structure 54 that is received (inserted) in a guide path structure 68 of the outer cylinder 40 as illustrated in FIG. 1 so as to operate the inner cylinder 36 and the outer cylinder 40. The projection 52 is formed in an isosceles triangle shape in side view, having two base corner portions 52*a* at the axial direction distal end and the proximal end of the annular portion 46, and having one apex corner portion 52*b* at an intermediate portion in the axial direction, shifted from the two base corner portions 52*a* in the circumferential direction (rightward). The base corner portion 52*a* and the apex corner portion 52*b* are R-chamfered. The projection 52 has a proximal end inclined side 52*c* and a distal end inclined side 52*d* inclined with respect to the circumferential direction, formed by connecting the apex corner portion 52*b* and the base corner portions 52*a*.

Returning to FIGS. 2 and 3, the spring 38 of the protective device 14 is configured as a coil spring having an outer diameter smaller than that of the outer cylinder 40, and is accommodated in the outer cylinder 40. The spring 38 internally accommodates the needle 16 and the protruding wall portion 48 of the inner cylinder 36 and is disposed between the annular portion 46 of the inner cylinder 36 and an upper bottom wall 58 of the outer cylinder 40. The spring 38 elastically expands and contracts along the axial direction of the protective device 14 and biases in a direction to separate the inner cylinder 36 and the upper bottom wall 58 of the outer cylinder 40 away from each other in a contracted state.

Figure 5A:
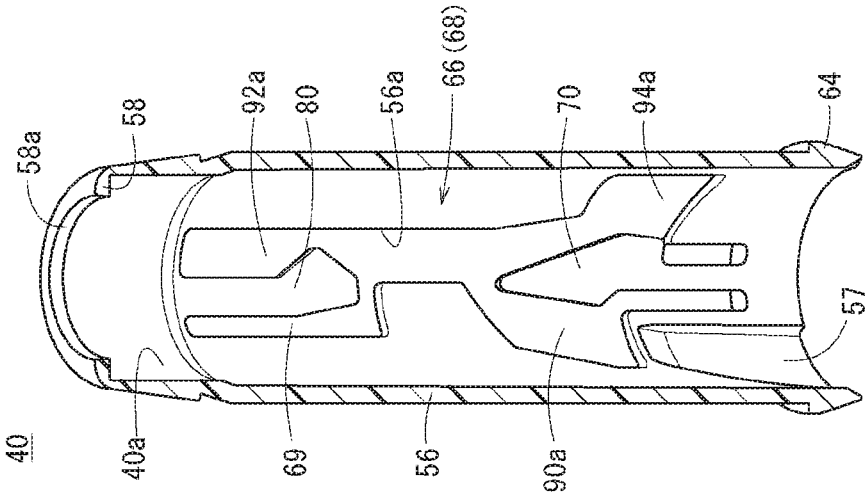
FIG. 5A is an enlarged side view of an outer cylinder of FIG. 1.
Figure 5B:
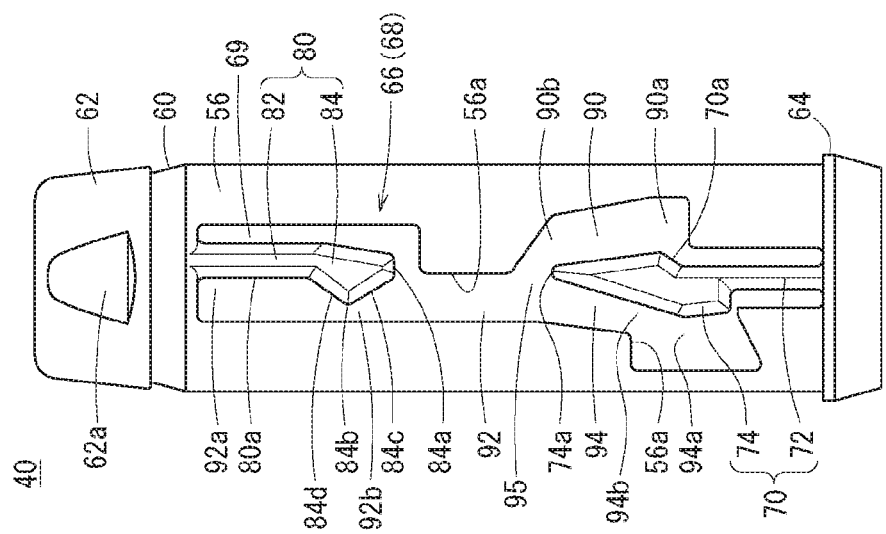
FIG. 5B is a side sectional view of the outer cylinder of FIG. 5A.

The outer cylinder 40 of the protective device 14 is formed in an outer diameter slightly larger than the barrel portion 24 of the main body 18. The outer cylinder 40 internally includes a hollow portion 40*a*. The hollow portion 40*a* accommodates the needle 16, the distal side of the main body 18, the inner cylinder 36, and the spring 38. Furthermore, as illustrated in FIGS. 5A and 5B, the outer cylinder 40 has a cylindrical peripheral wall 56 and the upper bottom wall 58 continuous with the distal end of the peripheral wall 56 and protruding slightly inward in the radial direction.

The peripheral wall 56 surrounds a side periphery of the hollow portion 40*a*, and its axial direction length is longer than the entire length of the needle 16. The inner diameter of the peripheral wall 56 is set to be slightly larger than the outer diameter of the barrel portion 24 so as to achieve both smooth relative movement of the outer cylinder 40 and the miniaturization of the protective device 14. A pair of guide grooves 57 for guiding the projections 52 of the inner cylinder 36 to an initial position 90*a* to be described below at assembly of the protective device 14 is provided on the inner surface of the peripheral wall 56.

The upper bottom wall 58 is formed in an annular fashion at the distal end of the peripheral wall 56, and its proximal end surface is a seat on which a tip of the spring 38 is disposed. A distal end opening 58*a* communicating with the hollow portion 40*a* and exposing the needle 16 at the time of puncture is formed at the distal end of the outer cylinder 40 by a peripheral edge of the upper bottom wall 58.

An annular recess 60 for preventing disengagement of the cover 42 in the distal direction extends in the circumferential direction on the outer circumferential surface on the distal side of the peripheral wall 56. The peripheral wall 56 on the distal side of the annular recess 60 is a distal end tapered portion 62 being slightly narrowed in the distal direction. The outer circumferential surface of the distal end tapered portion 62 includes a pair of flat surfaces 62*a* used for rotational alignment with the guide groove 57 when the inner cylinder 36 is inserted into the outer cylinder 40. Furthermore, a flange portion 64 protrudes outward in the radial direction on the outer circumferential surface on the proximal side of the peripheral wall 56. The flange portion 64 reinforces the proximal end portion of the outer cylinder 40 and restricts disengagement of the cover 42 in the proximal direction.

The peripheral wall 56 includes the guide path structure 68 for guiding the cam structure 54 (pair of projections 52) of the inner cylinder 36 between the vicinity of the flange portion 64 and the annular recess 60. The guide path structure 68 is configured with a pair of guide paths 66 that are rotationally offset by 180° in the circumferential direction of the peripheral wall 56, that is, provided to face each other across the hollow portion 40*a*.

The pair of guide paths 66 allows communication between the hollow portion 40*a* and the outside of the outer cylinder 40 and is formed to have a mutually same shape in development view of the peripheral wall 56. Each of the pair of projections 52 of the inner cylinder 36 is disposed separately on one side and the other side of the guide path 66. Moreover, a proximal side elastic piece 70 extending from the proximal end of the guide path 66 in the distal direction and a distal side elastic piece 80 (elastically deformable portion, click feeling generator) extending from the distal end of the guide path 66 in the proximal direction are provided inside the guide path 66.

The proximal side elastic piece 70 includes: an elastic rod portion 72 connected to the distal end of the flange portion 64 and protruding in the distal direction; and a tilting portion 74 connected to the distal end of the elastic rod portion 72 and having an arrow shape in plan view. The elastic rod portion 72 protrudes short from the flange portion 64 so as to dispose the tilting portion 74 in a relatively large space close to the proximal end of the guide path 66 to divide an initial passage 90 and a late passage 94 to be described below. Together with the contact with the cam structure 54, the proximal side elastic piece 70 causes the elastic rod portion 72 to elastically deform in the circumferential direction and causes the tilting portion 74 to tilt within the guide path 66.

In a similar manner, the distal side elastic piece 80 includes: an elastic rod portion 82 (elastically deformable main body) connected to the proximal end of the annular recess 60 and protruding in the proximal direction; and a tilting portion 84 (protruding portion) connected to the distal end portion of the elastic rod portion 82 and having a triangular shape in plan view. The elastic rod portion 82 includes: a distal end portion connected to the peripheral wall 56 of the outer cylinder 40; and a proximal end portion that is a free end, and extends from the distal end of the guide path 66 in the proximal direction along the axial direction of the cylinder 40 until it passes a puncture position 92*a*. The tilting portion 84 is an extended end portion of the distal side elastic piece 80 and is disposed at a position (slightly proximal side from the puncture position 92*a* described below) spaced to some extent from the distal end of the guide path 66 by the elastic rod portion 82. This arrangement generates a gap between the tilting portion 84 and the puncture position 92*a* so as to allow the projection 52 to move in the axial direction to some extent.

The tilting portion 84 includes: a proximal apex 84*a* (corner portion) in the proximal direction; and a side apex 84*b* on the guide path 66 side. Each of the apexes 84*a* and 84*b* is R-chamfered. A portion between the proximal apex 84*a* and the side apex 84*b* is a proximal end inclined edge portion 84*c* inclined toward the guide path 66 side in the distal direction. That is, the tilting portion 84 being a protruding portion includes, on its proximal side, a proximal side inclined surface having the amount of protrusion of the protruding portion to the guide path 66 gradually increasing in the distal direction. Moreover, a portion between the side apex 84b and a connection point of the elastic rod portion 82 is a distal end inclined edge portion 84d inclined toward the guide path 66 in the proximal direction. That is, the tilting portion 84 is a protruding portion that includes, on its distal side, a distal side inclined surface having the amount of protrusion of the protruding portion to the guide path 66 gradually increasing toward the proximal direction. In addition, the side apex 84b and the distal end inclined edge portion 84d of the tilting portion 84 function as a resistance force generator that generates a resistance force by contact with the projection 52. This resistance force is smaller than the biasing force of the spring 38 in a state where the projection 52 is positioned at the puncture position 92a described below.

A cutout portion 69 communicating with the guide path 66 is formed to extend along the distal side elastic piece 80 on the side opposite to the guide path 66 side of the distal side elastic piece 80 in order to enable the distal side elastic piece 80 to be elastically deformable in the circumferential direction. The tilting portion 84 of the distal side elastic piece 80 elastically deforms and tilts in the circumferential direction so as to allow the elastic rod portion 82 to separate from the guide path 66 together with the contact of the cam structure 54. The proximal apex 84a of the tilting portion 84 comes in proximity to a corner portion protruding from the peripheral wall 56 toward the guide path 66, restricting the projection 52 from entering the cutout portion 69.

The guide path 66 is formed to have the initial passage 90, an intermediate passage 92, and the late passage 94 by the edge portion 56a of the peripheral wall 56 and the edge portions 70a and 80a of the proximal side elastic piece 70 and the distal side elastic piece 80, respectively. The initial passage 90, the intermediate passage 92 and the late passage 94 communicate with each other at a merging position 95 in the vicinity of the distal apex 74a of the proximal side elastic piece 70 (distal direction of the distal apex 74a in FIG. 5A and on the late passage 94 side). In addition, the initial passage 90 and the intermediate passage 92 include a distal direction passage that guides the cam structure 54 from an initial position 90a (described below) to a puncture position 92a (described below) at the time of puncture. Furthermore, the intermediate passage 92 and the late passage 94 include a proximal direction passage that guides the cam structure 54 from the puncture position 92a (described below) to a final position 94a (described below) after the puncture.

In FIG. 5A, the initial passage 90 is an inclined passage extending diagonally leftwards in the distal direction on the right side of the proximal side elastic piece 70, and its proximal end portion is an initial position 90a where the projection 52 of the inner cylinder 36 is arranged before puncture of the needle 16. A width from the initial position 90a of the initial passage 90 to a predetermined range position in the distal direction is set to a width that enables easy movement of the projection 52 between the edge portion 56a of the peripheral wall 56 and the edge portion 70a of the proximal side elastic piece 70. The edge portion 56a of the peripheral wall 56 and the distal apex 74a of the proximal side elastic piece 70 come in proximity to each other, forming a portion of the initial passage 90 near the merging position 95 into a distal direction passage narrow portion 90b slightly narrower than the projection 52. In addition, as will be described below, the proximal side elastic piece 70 functions as a distal direction passage elastically deformable portion that prevents the cam structure 54 that has moved to the puncture position 92a from moving to the initial position 90a.

The intermediate passage 92 linearly extends in the distal direction from the merging position 95 in more toward the distal side than the proximal side elastic piece 70, with the distal end portion of the intermediate passage 92 defined as the puncture position 92a to which the projection 52 of the inner cylinder 36 moves at the time of puncture with the needle 16. Accordingly, the initial position 90a and the puncture position 92a are mutually rotationally offset in the circumferential direction. Furthermore, the intermediate passage 92 is formed to pass through the left side of the distal side elastic piece 80. Note that the intermediate passage 92 may be formed to pass through the right side of the distal side elastic piece 80. In this case, the distal side elastic piece 80 may be formed on the left side of the intermediate passage 92 and the side apex 84b of the distal side elastic piece 80 may be formed to protrude on the right side.

A width from the merging position 95 of the intermediate passage 92 to the distal side elastic piece 80 is set to a width that enables easy movement of the projection 52 between the edge portions 56a of the peripheral wall 56. At a location where the tilting portion 84 of the distal side elastic piece 80 protrudes toward the guide path 66, protruding portion of the side apex 84b, the distal end inclined edge portion 84d, and the proximal end inclined edge portion 84c, that is, protruding portion of the inclined portion 84 as a protruding portion into the guide path 66 leads to formation of the intermediate passage narrow portion 92b slightly narrower than the projection 52 within the guide path 66. A portion distal of the tilting portion 84 (including the puncture position 92a) is set to a width that enables easy movement of the projection 52 between the edge portion 56a of the peripheral wall 56 and the edge portion 80a of the distal side elastic piece 80.

The late passage 94 extends diagonally leftward from the merging position 95 in the proximal direction on the left side of the proximal side elastic piece 70, with the proximal end portion of the late passage 94 defined as a final position 94a to which the projection 52 of the inner cylinder 36 moves after puncture with the needle 16. Moreover, the late passage 94 has a portion between the edge portion 56a of the peripheral wall 56 and the edge portion 70a of the proximal side elastic piece 70 gradually narrowing in the proximal direction, forming a proximal direction passage narrow portion 94b narrower than the projection 52 at the front of the final position 94a. Elastic deformation of the proximal side elastic piece 70 by its contact with the projection 52 enables the proximal direction passage narrow portion 94b to be expanded to a width that allows passage of the projection 52.

Furthermore, the final position 94a is formed in a shape that would not cause the guided projection 52 to be disengaged from the final position 94a. Specifically, the edge portion 56a on the distal side facing the final position 94a extends in parallel in the circumferential direction and reaches the proximal direction passage narrow portion 94b, making it possible to prevent the distal end inclined side 52d of the projection 52 from entering the proximal direction passage narrow portion 94b of the late passage 94. Furthermore, the tilting portion 74 of the proximal side elastic piece 70 extends to the side portion of the final position 94a, enabling the proximal side elastic piece 70 to elastically push the cam structure 54 that comes in contact with the projection 52 and is going to move from the final position 94a toward the proximal direction passage narrow portion 94b back to the final position 94a side.

The above guide path structure 68 guides each of the projections 52 of the received inner cylinder 36 so as to be present at the same position of the pair of guide paths 66. The initial passage 90 and the intermediate passage 92 constitute the distal direction passage that guides the projection 52 from the initial position 90a to the puncture position 92a at the time of puncture. The intermediate passage 92 and the late passage 94 constitute the proximal direction passage that guides the projection 52 from the puncture position 92a to the final position 94a after the puncture. With this configuration, relative movement and relative rotation of the inner cylinder 36 with respect to the outer cylinder 40 are stably performed.

Returning to FIGS. 2 and 3, the cover 42 is configured to be attached to the peripheral wall 56 of the outer cylinder 40 to cover (hide) the guide path structure 68. The distal side of the cover 42 includes a plurality of inclined pieces 42a inclined inward in the radial direction to be caught by the annular recess 60. The axial direction length of the cover 42 matches the length from the flange portion 64 of the outer cylinder 40 to the annular recess 60, making it possible to cover the entire guide path structure 68. The outer diameter of the cover 42 substantially matches the outer diameter of the flange portion 64. With the presence of the cover 42, the protective device 14 can prevent the user from inadvertently touching the cam structure 54 or the guide path structure 68, leading to enhancement of safety.

In addition, the cap 44 is formed in a tubular shape having a needle housing space 44a (refer to FIG. 3) by a flexible resin material. A portion on more distal side than the needle housing space 44a of the cap 44 is a thick portion, and this thick portion is punctured with the needle tip 16a of the needle 16 to seal the needle tip 16a. A projecting piece 45 that can be caught on the upper bottom wall 58 constituting the distal end opening 58a of the protective device 14 is provided on the outer circumferential surface of the cap 44.

The proximal side of the cap 44 comes into contact with the inner cylinder 36 of the protective device 14 in a state where the cap 44 is attached to the needle holding portion 28 so as to suppress the operation of the inner cylinder 36 before use, and together with this, closely adheres to the outer circumferential surface of the bulging tube portion 32. While maintaining the needle 16 to an unexposed state until use of the medical instrument assembly 10, the cap 44 allows a disc portion 44b spreading outward in the radial direction on the distal side to be exposed from the distal end opening 58a of the outer cylinder 40. At the use of the medical instrument assembly 10, the disc portion 44b is pinched and pulled out by the user in the distal direction, disengaging the projecting piece 45 and the upper bottom wall 58 from each other so as to allow the cap 44 to be removed.

The protective device 14 and the medical instrument assembly 10 according to the first embodiment are basically configured as described above. Operation and effects thereof will be specifically described below.

The medical instrument assembly 10 is provided in a state where the storage space 18a is filled with a medicinal solution and the storage space 18a is sealed with the gasket 20. Furthermore, as illustrated in FIG. 3, the medical instrument assembly 10 includes the cap 44 inserted in the outer cylinder 40 to prevent exposure of the needle 16 and leakage of the medicinal solution.

The medical instrument assembly 10 is provided with the plunger 22 attached to the gasket 20 and a jig 96 (refer to FIG. 7A) on which the user hooks one's finger, attached on the main body 18. At use of the medical instrument assembly 10, the user pulls out the cap 44 from the protective device 14. This proceeds to a state before puncture, that is, a state of the medical instrument assembly 10 capable of puncturing and medicinal solution administration onto the patient. In the state before puncture, as illustrated in FIG. 6A, the cam structure 54 (pair of projections 52) of the inner cylinder 36 is positioned at the initial position 90a of the guide path structure 68 (pair of guide paths 66) of the outer cylinder 40. Note that FIGS. 6A to 6D and 7B omit illustration of the cover 42 in order to facilitate understanding of the described embodiment.

At the time of puncture with the needle 16, the user brings the distal end surface of the outer cylinder 40 into contact with a puncture site (arms, etc.) of the patient and fixes the surface so as to allow the syringe 12 to advance with respect to the outer cylinder 40. That is, the user pushes on the syringe 12 toward the puncture target. This operation moves the needle 16, the main body 18, and the inner cylinder 36 to be displaced relative to the outer cylinder 40 and the cover 42 in the distal direction, allowing the spring 38 in the outer cylinder 40 to contract in the axial direction. Then, the needle 16 is gradually exposed from the distal end opening 58a of the outer cylinder 40.

In addition, with the advance of the inner cylinder 36 relative to the outer cylinder 40, the projection 52 of the inner cylinder 36 advances from the initial position 90a as a standby position and passes through the initial passage 90 as one of the distal direction passages of the guide path 66 to move in the distal direction as illustrated in FIG. 6B. The inner cylinder 36 rotatably attached to the needle holding portion 28 rotates in the circumferential direction as the projection 52 is guided through the initial passage 90. More specifically, the projection 52 moves diagonally toward the distal end in the initial passage 90 and reaches the distal direction passage narrow portion 90b. Then, the projection 52 elastically deforms the proximal side elastic piece 70 toward the final position 94a side so as to expand the distal direction passage narrow portion 90b, and passes through the distal direction passage narrow portion 90b. After passage of the projection 52, the proximal side elastic piece 70 elastically returns to its original posture.

Along with advancement of the inner cylinder 36 with respect to the outer cylinder 40, the projection 52 enters the merging position 95, goes straight in the distal direction from the merging position 95 through the intermediate passage 92 functioning as a portion of the distal direction passage, passing through the intermediate passage narrow portion 92b. At the intermediate passage narrow portion 92b, the distal end inclined side 52d of the projection 52 comes in contact with the proximal end inclined edge portion 84c of the distal side elastic piece 80 to elastically deform the distal side elastic piece 80 toward the side opposite to the side of the guide path 66 so as to expand the intermediate passage narrow portion 92b. When the projection 52 passes the side apex 84b, the distal side elastic piece 80 vibrates due to the elastic restoration, and this vibration is perceived by the user as a click feeling. Specifically, the click feeling is transmitted to the audio sense of the user by sound, or transmitted as vibration to the tactile sense of the user grasping the device via the medical instrument assembly 10.

As illustrated in FIG. 6C, the needle 16 is sufficiently exposed from the distal end opening 58a of the outer cylinder 40 when the projection 52 passes the intermediate passage narrow portion 92b. That is, the user can recognize that the sufficient exposure of the needle 16 by the click feeling. Furthermore, the projection 52 passes through the intermediate passage narrow portion 92b and thereafter, the projection 52 advances slightly in the distal direction and reaches the puncture position 92a. In this state, the needle 16 exposed from the outer cylinder 40 has punctured the patient's body.

Figure 7A:
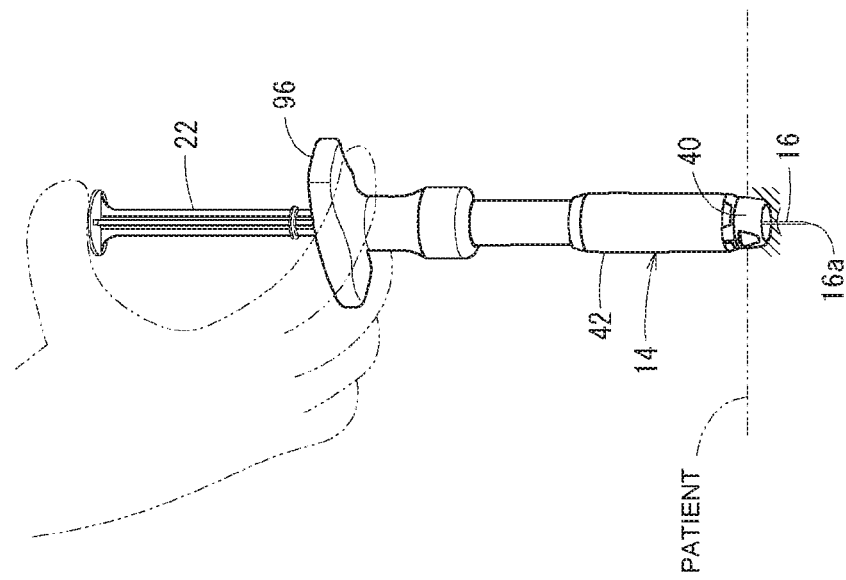
FIG. 7A is an explanatory view illustrating a state in which a medicinal solution is administered from a medical instrument assembly as fourth operation following FIG. 6C.

As illustrated in FIG. 7A, in the puncturing state of the needle 16, the user depresses the plunger 22 to discharge the medicinal solution in the storage space 18a from the distal end of the needle 16 for administration. Here, because the spring 38 is contracted in the outer cylinder 40 in the puncturing state, the syringe 12 including the inner cylinder 36 and the needle 16 is biased in the proximal direction (direction in which the needle 16 escapes) relative to the outer cylinder 40. Therefore, when medicinal solution is administered, the user needs to keep pushing the syringe 12 toward the puncture target. Meanwhile, the force used for the pressing operation of the plunger 22 is applied in a direction to release the syringe 12 from the puncture target, decreasing the user's force to push the syringe 12 toward the puncture target. Therefore, with the conventional protective device, the user's force to push the syringe 12 toward the puncture target easily falls below the biasing force of the spring 38 to bias the syringe 12 in the proximal direction, leading to a possibility of instantaneous retraction of the inner cylinder 36 and the syringe 12 biased by the spring 38, and leading to a possibility of detachment of the needle 16 from the patient in some cases.

Figure 7B:
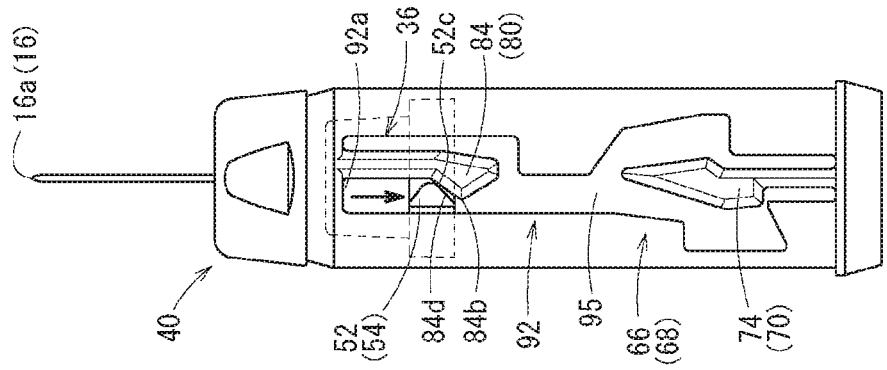
FIG. 7B is a partial side view illustrating fourth operation in FIG. 7A.

In contrast, as illustrated in FIG. 7B, in the protective device 14 according to the present embodiment has a configuration to generate a resistance force against the relative movement of the inner cylinder 36 in the proximal direction, with respect to the outer cylinder 40 by the biasing force of the spring 38 by the contact between the tilting portion 84 of the distal side elastic piece 80 and the projection 52. Specifically, this resistance force is generated by the contact of the proximal end inclined side 52c of the projection 52 located at the puncture position 92a or the vicinity thereof with the distal end inclined edge portion 84d of the tilting portion 84. Therefore, even when the retraction force of the inner cylinder 36 with respect to the outer cylinder 40 decreased and the user's force to push the medical instrument assembly 10 toward the puncture target is somewhat lower than the biasing force of the spring 38 at the time of administration of medicinal solution, it is possible to suppress retraction of the inner cylinder 36 with respect to the outer cylinder 40. As a result, it is possible to suppress disengagement of the needle 16 from the patient at a pressing operation of the plunger 22, enabling the user to administer the medicinal solution satisfactorily.

After administration of the medicinal solution, the user separates the medical instrument assembly 10 away from the skin in order to withdraw the needle 16 from the patient. With this operation, the outer cylinder 40 and the cover 42 are pushed by the spring 38 and move in the distal direction relative to the needle 16, the main body 18, and the inner cylinder 36. Here, the resistance force generated by the contact between the tilting portion 84 of the distal side elastic piece 80 and the projection 52 is smaller than the biasing force of the spring 38 when the projection 52 (cam structure 54) is positioned at the puncture position 92a, and thus, the projection 52 directed from the puncture position 92a in the proximal direction reliably overcomes the tilting portion 84 which is a protruding portion functioning as a resistance force generator. Thereafter, the projection 52 linearly moves along the intermediate passage 92 functioning as a portion of the proximal direction passage with substantially no rotation of the inner cylinder 36, and moves in the late passage 94 as a portion of the proximal direction passage. Note that the proximal end inclined side 52c comes in contact with the edge portion 70a of the tilting portion 74 at the merging position 95, the projection 52 is restricted from entering the initial passage 90 and guided to the late passage 94. In this manner, the proximal side elastic piece 70 functions as a distal direction passage elastically deformable portion that prevents the cam structure 54 that has moved to the puncture position 92a from moving to the initial position 90a.

The projection 52 is guided leftward in the proximal direction in the late passage 94, whereby the inner cylinder 36 rotates with respect to the outer cylinder 140. Then, the projection 52 moves to the proximal direction passage narrow portion 94b and elastically deforms the proximal side elastic piece 70 so as to expand the proximal direction passage narrow portion 94b and passes through the proximal direction passage narrow portion 94b, and then, is guided to the final position 94a as illustrated in FIG. 6D. At a stage where the projection 52 has moved to the final position 94a, the relative movements of the needle 16, the main body 18, and the inner cylinder 36 with respect to the outer cylinder 40 are completed, and the needle 16 is accommodated in the outer cylinder 40.

The protective device 14 prevents re-exposure of the needle 16 when the projection 52 has moved to the final position 94a. That is, because the edge portion 56a of the peripheral wall 56 is opposed to the distal end of the projection 52, even in a case where the needle 16 and the inner cylinder 36 are re-advanced in the distal direction relative to the outer cylinder 40, the projection 52 would be caught by the edge portion 56a, restricting the movement in the distal direction.

As described above, the protective device 14 and the medical instrument assembly 10 according to the present embodiment includes the tilting portion 84 of the distal side elastic piece 80 that generates a resistance force against the relative movement of the inner cylinder 36 in the proximal direction with respect to the outer cylinder 40 by the biasing force of the spring 38 at the puncture position 92a or in the vicinity of the puncture position 92a. With this configuration, it is possible to reduce the retraction force of the inner cylinder 36 with respect to the outer cylinder 40 due to the biasing force of the spring 38 in the exposed state of the needle 16. For example, the retraction force of the inner cylinder 36 with respect to the outer cylinder 40 is suppressed by the resistance force even when a force of a user pressing the syringe 12 onto the patient as the puncture target is decreased with the pushing operation of the plunger 22 at the time of administration of the medicinal solution, making it possible to suppress inadvertent retraction of the inner cylinder 36 with respect to the outer cylinder 40. Accordingly, it is possible to satisfactorily suppress the disengagement of the needle 16 from the patient. Furthermore, with the cam structure 54 guided to the puncture position 92a that is rotationally offset in the circumferential direction from the initial position 90a, it is possible to avoid an inconvenience that when the cam structure 54 guided to the puncture position 92a retracts in the proximal direction, the cam structure 54 returns to the initial position 90a and can be re-exposed. This enables the protective device 14 to further enhance handleability. In addition, the resistance force of the resistance force generator is set to be smaller than the biasing force of the spring 38 in a state where the projection 52 is located at the puncture position 92a. Therefore, due to the biasing force of the spring 38 after the puncture, the projection 52 of the cam structure 54 can pass through the side apex 84b and the distal end inclined edge portion 84d of the tilting portion 84, which is the resistance force generator, and can reliably reach the final position 94*a*. Note that the vicinity of the puncture position 92*a* is a position where the projection 52 is positioned when the needle 16 is exposed by a minimum length in order to puncture to a predetermined depth with the needle 16.

In addition, the initial passage 90, which is a portion of the distal direction passage, is an inclined passage extending diagonally toward the distal direction, and the proximal direction passage configured with the intermediate passage 92 and the late passage 94 is linearly located along the axial direction of the outer cylinder 40 from the vicinity of the proximal end of the puncture position 92*a* to the proximal side elastic piece 70 functioning as the proximal direction passage elastically deformable portion. With this configuration, there is substantially no portion, other than the resistance force generator, that reduces the retraction force of the inner cylinder 36 with respect to the outer cylinder 40 between the vicinity of the proximal end of the puncture position 92*a* and the proximal direction passage narrow portion 94*b*, making it possible to allow the projection 52 to easily pass through the proximal direction passage narrow portion 94*b* while elastically deforming the proximal side elastic piece 70 on the basis of the biasing force of the spring 38. Accordingly, the cam structure 54 guided to the puncture position 92*a* can be reliably moved to the final position 94*a* on the basis of the biasing force of the spring 38. Furthermore, with the presence of the proximal side elastic piece 70 functioning as the distal direction passage elastically deformable portion that prevents the cam structure 54 that has moved to the puncture position 92*a* from moving to the initial position 90*a*, it is possible to reliably move the cam structure 54 from the puncture position 92*a* to the final position 94*a*.

Moreover, because the guide path 66 includes the tilting portion 84 of the distal side elastic piece 80 that can come in contact with the proximal end inclined side 52*c* of the cam structure 54 that has moved to the puncture position 92*a* or the vicinity thereof, it is possible to easily generate a resistance force on the cam structure 54 that has moved to the puncture position 92*a*. In addition, the distal side elastic piece 80 includes: the elastic rod portion 82 connected to the peripheral wall 56 of the outer cylinder 40; and the tilting portion 84 protruding into the guide path 66 from the elastic rod portion 82. With this configuration, it is possible to generate a resistance force in the inner cylinder 36 by the contact between the tilting portion 84 and the projection 52, while easily allowing the movement of the cam structure 54 from the puncture position 92*a* in the proximal direction by the elastic deformation of the elastic rod portion 82. Furthermore, the tilting portion 84 including the distal end inclined edge portion 84*d* has the proximal side width of the puncture position 92*a* smaller than the width of the projection 52, making it possible to achieve reliable contact with the projection 52 moving in the guide path 66 and generate a resistance force. At this time, with the presence of the distal end inclined edge portion 84*d* included in the tilting portion 84, it is possible to easily elastically deform the elastic rod portion 82 in the circumferential direction of the outer cylinder 40 by the contact of the cam structure 54 with the distal end inclined edge portion 84*d*. Furthermore, with the configuration in which the distal side elastic piece 80 extends from the distal end of the guide path 66 in the proximal direction, it is possible to increase the elastic force with reduced length of extension. This makes it possible to increase the resistance force generated in the cam structure 54 and further reduce the retraction force of the inner cylinder 36 with respect to the outer cylinder 40. Note that it is preferable that the resistance force is 10 to 50% of the biasing force of the spring 38 in a state where the projection 52 is positioned at the puncture position 92*a*. With this arrangement, it is possible to sufficiently reduce inadvertent retraction of the inner cylinder 36 with respect to the outer cylinder 40, and possible to cause the cam structure 54 positioned at the puncture position 92*a* to reliably move to the final position 94*a* through the resistance force generator.

In addition, with the distal side elastic piece 80 that generates a click feeling with the passage of the cam structure 54 provided in the protective device 14 and the medical instrument assembly 10, it is possible to allow the user to recognize that the needle 16 is sufficiently exposed from the outer cylinder 40. In addition, because the distal side elastic piece 80 is provided in the vicinity of the proximal end of the puncture position 92*a*, the cam structure 54 can be located at the puncture position 92*a* that is rotationally offset from the initial position 90*a* in the circumferential direction immediately after user senses the click feeling or simultaneously with the sensing. Therefore, it is possible to prevent the cam structure 54 from returning from the puncture position 92*a* to the initial position 90*a* after the user senses a click feeling. That is, the protective device 14 can guide the projection 52 satisfactorily along the guide path 66 while enabling the user to sense the exposure of the needle 16 from the outer cylinder 40, making it possible to further improve the handleability of the protective device 14.

In this case, with generation of the click feeling by the elastic return of the distal side elastic piece 80, it is possible to easily provide the click feeling generator in the guide path structure 68, thereby simplifying the device. In addition, this makes it possible to reliably allow the elastic rod portion 82 to elastically deform in the circumferential direction of the outer cylinder 40 by the contact between the tilting portion 84 and the cam structure 54, and to generate a reliable click feeling at the time of elastic return of the elastic rod portion 82. At this time, with the presence of the proximal end inclined edge portion 84*c* included in the tilting portion 84, it is possible to easily elastically deform the elastic rod portion 82 in the circumferential direction of the outer cylinder 40 by the contact of the cam structure 54 with the proximal end inclined edge portion 84*c*.

Furthermore, while a configuration in which the cover 42 covers the outer cylinder 40 would make it difficult to easily recognize the position of the projection 52 and to grasp the exposed state of the needle 16, it is possible to notify the user of the sufficiently exposed needle 16 with a click feeling generated together with the movement of the projection 52.

With preparation of the medical instrument assembly 10 in which the protective device 14 has been attached to the syringe 12, the user can immediately use the medical instrument assembly 10, with further enhanced usability.

Note that the protective device 14 and the medical instrument assembly 10 according to the present invention are not limited to the above-described embodiments, and may be implemented in various modes. For example, the number of projections 52 to be formed in the cam structure 54 and the number of the guide paths 66 to be formed in the guide path structure 68 are not particularly limited, and may be one, or three or more. Furthermore, the pair of projections 52 and the pair of guide paths 66 may be provided at any position in the circumferential direction rather than position to face each other across the hollow portion 40*a*. Furthermore, the protective device 14 may omit the cover 42, or may provide the cover 42 integrally molded with the outer cylinder 40 (having a groove corresponding to the guide path 66 on the inner surface). Still further, the medical instrument assembly 10 may be provided in a state where the protective device 14 and the cap 44 have been attached to the main body 18 not filled with the medicinal solution. In this case, the storage space 18a would be filled with the medicinal solution at an implementation site, and thereafter the gasket 20 would be capped, then the plunger 22 would be attached to complete production of the medical instrument assembly 10 filled with the medicinal solution.

Second Embodiment

Next, a medical instrument assembly 110 and a protective device 114 according to a second embodiment will be described with reference to FIGS. 8A to 12D. In the following description, the same reference numerals are given to components having the same configuration or the same functions as those of the medical instrument assembly 10 according to the first embodiment, and a detailed description thereof will be omitted. In addition, the following FIGS. 8A to 16B omit illustration of the cover 42 and the cap 44 to facilitate understanding of the described embodiment.

As illustrated in FIGS. 8A and 8B, the protective device 114 of the medical instrument assembly 110 according to the second embodiment has a guide path structure 168 in an outer cylinder 140, different from the guide path structure 68 according to the first embodiment. Specifically, the guide path structure 168 is configured with a first guide path 170 and a second guide path 180 having mutually different shapes, and guides the cam structure 54 (pair of projections 52) of the inner cylinder 36.

The first guide path 170 internally includes: an extending elastic portion 172 (distal direction passage elastically deformable portion, a click feeling generator) extending long from the proximal end of the first guide path 170 in the distal direction; and a side elastic portion 174 (proximal direction passage elastically deformable portion) extending in the proximal direction and protruding from an edge portion 156a (edge portion constituting a first late passage 178) of a peripheral wall 156 extending along the axial direction of the outer cylinder 140. The extending elastic portion 172 includes: a substantially triangular shaped connection 172a continuous to the peripheral wall 156 of the outer cylinder 140 and gradually narrowing in the distal direction; a straight rod portion 172b (elastically deformable main body) having a proximal end portion continuing to the distal end of the connection 172a and having a distal end portion linearly extending and being a free end; and a guide projecting portion 173 (protruding portion) provided at the distal end of the straight rod portion 172b. The connection 172a and the straight rod portion 172b extend long to the vicinity of the distal end of the first guide path 170. The guide projecting portion 173 curves diagonally from the straight rod portion 172b toward the distal side and has a distal apex 173a in the distal direction and a side apex 173b on the first late passage 178 side. A portion between the distal apex 173a and the side apex 173b is a distal end inclined edge portion 173c inclined leftward in the proximal direction. That is, the guide projecting portion 173 is a protruding portion that includes, on its distal side, a distal side inclined surface having the amount of protrusion of the protruding portion to the first guide path 170 gradually increasing toward the proximal direction. The distal apex 173a, the side apex 173b, and the distal end inclined edge portion 173c function as a resistance force generator that generates a resistance force on the projection 52.

Meanwhile, the side elastic portion 174 includes: a connection 174a extending long along the left side of the peripheral wall 156; a curved rod portion 174b connected to the proximal end of the connection 174a and extending curvedly in the proximal direction; and a lock projecting portion 174c provided at the proximal end of the curved rod portion 174b. The curved rod portion 174b curvedly protrudes so as to separate from the edge portion 156a of the peripheral wall 156 to narrow the first guide path 170. In order to prevent disengagement of the projections 52 guided by a first final position 178a described below, the lock projecting portion 174c has a substantially triangular shape having corner portions in the proximal direction and the direction opposite to the direction into the first late passage 178.

The first guide path 170 is formed to include a first initial passage 176 and a first late passage 178 by an edge portion 156a of the peripheral wall 156, an edge portion 171 of the extending elastic portion 172, and an edge portion 175 of the side elastic portion 174. The first initial passage 176 and the first late passage 178 communicate with each other at the distal side (a first puncture position 177) of the first guide path 170.

The first initial passage 176 is a space on one side divided in the circumferential direction of the outer cylinder 140 by the extending elastic portion 172 and is an inclined passage diagonally extending toward a space in the distal direction and on the other side. The first initial passage 176 includes, at proximal end thereof, a first initial position 176a at which the projection 52 is disposed in the initial state, and includes, at its distal end, a first puncture position 177 to which the projection 52 is guided at the time of puncture with the needle 16. The first initial position 176a and the first puncture position 177 are rotationally offset in the circumferential direction. A width from the first initial position 176a of the first initial passage 176 to the first puncture position 177 is set to a width that enables easy movement of the projection 52 between the edge portion 156a of the peripheral wall 156 and the edge portion 171 of the extending elastic portion 172.

Meanwhile, the first late passage 178 is the other space divided in the circumferential direction of the outer cylinder 140 by the extending elastic portion 172, and extends from the first puncture position 177 in the proximal direction, so as to allow communication between the above-described first puncture position 177 and a first final position 178a to which the projection 52 is guided after puncture with the needle 16. A portion on more proximal side on the first late passage 178 than the first puncture position 177 is slightly inclined diagonally into the first late passage 178 due to the formation of the side elastic portion 174. Moreover, the curved rod portion 174b and the lock projecting portion 174c diagonally protrude into the first late passage 178 at the front of the first final position 178a, so as to form a proximal direction passage narrow portion 178b narrower than the projection 52.

The first final position 178a is formed in a shape to suppress disengagement of the guided projection 52 from the first final position 178a. Specifically, the first final position 178a is formed by cutting out the peripheral wall 156 into a relatively large space to arrange the projection 52. The lock projecting portion 174c of the side elastic portion 174 forms the proximal direction passage narrow portion 178b narrower than the distal end inclined side 52d of the projection 52 so as to narrow an entrance of the first final position 178a. With this configuration, when the projection 52 moves in the distal direction, the inclined portion on the proximal side of the lock projecting portion 174c comes into contact with the distal end inclined side 52d of the projection 52 so as to elastically push the projection 52 back to the first final position 178a.

As illustrated in FIG. 8B, the second guide path 180 of the guide path structure 168 internally includes an extending rigid portion 182 extending from the proximal end to a substantially intermediate portion in the axial direction of the second guide path 180. The extending rigid portion 182 is formed in a substantially triangular shape continuous with the peripheral wall 156 of the outer cylinder 140 and gradually narrowing in the distal direction. In addition, the second guide path 180 is formed to include a second initial passage 184 and a second late passage 186 by the edge portion 156a of the peripheral wall 156 and an edge portion 183 of the extending rigid portion 182 and include a second intermediate passage 188 on the distal side of the extending rigid portion 182. The second initial passage 184, the second late passage 186, and the second intermediate passage 188 communicate with each other at a merging position 189 closer to the distal side of the second guide path 180.

The second initial passage 184 is a space on one side divided in the circumferential direction of the outer cylinder 140 by the extending rigid portion 182 and diagonally extends toward a space in the distal direction and on the other side. The second initial passage 184 includes a second initial position 184a closer to the proximal end of the second guide path 180. A width of the second initial passage 184 is set to a width that enables easy movement of the projection 52 from the second initial position 184a to the merging position 189.

The second intermediate passage 188 linearly extends in the distal direction from the merging position 189 in a width that enables easy movement of the projection 52 and includes a second puncture position 188a at the most distal side.

The second late passage 186 is a space on the other side divided in the circumferential direction of the outer cylinder 140 by the extending rigid portion 182, and extends in the proximal direction to allow communication between the merging position 189 and a second final position 186a. The second late passage 186 also extends linearly with a width that enables easy movement of the projection 52. Moreover, the second final position 186a is formed to be wider in a direction opposite to the direction from the linear portion of the second late passage 186 into the second late passage 186, with the edge portion 156a of the peripheral wall 156 on the distal side thereof inclined diagonally on the distal side in a direction away from the second late passage 186.

Figure 9:
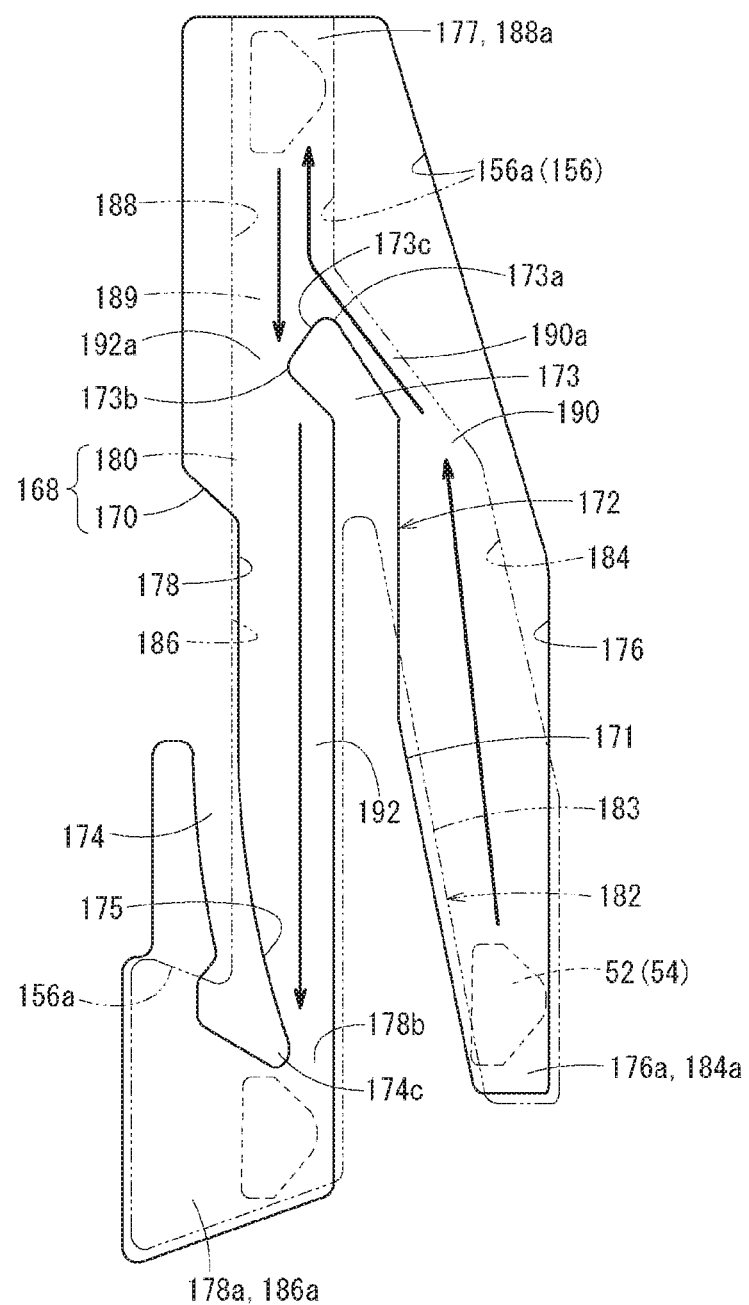
FIG. 9 is an explanatory view illustrating first and second guide paths of the outer cylinder of FIG. 8A in overlapped states.

The first and second guide paths 170 and 180 cooperate with each other to form a guide path structure 168 that allows the cam structure 54 (pair of projections 52) to pass through a predetermined path at the time of puncture with the needle 16. Specifically, as viewed in virtual superimposition of the first and second guide paths 170 and 180 as illustrated in FIG. 9, the structure has a portion in which the peripheral wall 156 constituting the second guide path 180 and an edge portion 183 of the extending rigid portion 182 are present inside the edge 156a of the peripheral wall 156 constituting the first guide path 170, the edge portion 171 of the extending elastic portion 172, and the edge portion 175 of the side elastic portion 174. In FIG. 9, the first guide path 170 is indicated by a solid line, and the second guide path 180 is indicated by a two-dot chain line.

That is, the guide path structure 168 includes a distal direction passage 190 as a practical path that guides each of the pair of projection 52 from the first and second initial positions 176a and 184a to the first and second puncture positions 177 and 188a at the time of puncture with the needle 16. The distal direction passage 190 is configured with the first initial passage 176 of the first guide path 170, and the second initial passage 184 and the second intermediate passage 188 of the second guide path 180. The distal direction passage 190 includes a distal direction passage narrow portion 190a in front of the merging position 189 of the second guide path 180. The distal direction passage narrow portion 190a is configured with the edge portion 171 of the extending elastic portion 172 (guide projecting portion 173) of the first guide path 170 and an edge portion 156a of the peripheral wall 156 of the second guide path 180. The distal direction passage 190 other than the distal direction passage narrow portion 190a is set to have a width at which the projection 52 is just movable.

In addition, the guide path structure 168 includes a proximal direction passage 192 that guides the pair of projections 52 from the first and second puncture positions 177 and 188a to the first and second final positions 178a and 186a after puncture. The proximal direction passage 192 is configured with the first late passage 178 of the first guide path 170 and the second intermediate passage 188 and the second late passage 186 of the second guide path 180. The proximal direction passage 192 includes a proximal direction passage narrow portion 192a on the proximal side of the merging position 189 of the second guide path 180. The proximal direction passage narrow portion 192a narrows the width of the second intermediate passage 188 by the guide projecting portion 173 of the extending elastic portion 172 projecting into the first late passage 178. The proximal direction passage 192 has a width that just allows linear movement of the projection 52, except for the proximal direction passage narrow portion 192a and the proximal direction passage narrow portion 178b of the first guide path 170.

The distal end inclined edge portion 173c of the guide projecting portion 173 comes in contact with the projection 52 when the projection 52 moves in the proximal direction from the first and second puncture positions 177 and 188a, and generates a resistance force on the projection 52. In addition, due to the formation of the distal direction passage narrow portion 190a, the extending elastic portion 172 is elastically deformed by the contact of the projection 52 when it passes, and a vibration (click feeling) is generated at elastic return of the projection 52 after passing so as to allow the user to perceive the movement of the projection 52 to the first and second puncture positions 177 and 188a.

The medical instrument assembly 110 and the protective device 114 according to the second embodiment are basically configured as described above. Operation and effects thereof will be described below.

Similarly to the medical instrument assembly 10 and the protective device 14 according to the first embodiment, the medical instrument assembly 110 and the protective device 114 move the cam structure 54 along the guide path structure 168 at the time of puncture by the user with the needle 16. That is, as illustrated in FIGS. 10A and 10B, the cam structure 54 (pair of projections 52) moves by advancement of the syringe 12 from the first and second initial positions 176a and 184a as standby positions toward the distal direction through the distal direction passage 190 of the guide path structure 168. This movement rotates the inner cylinder 36 relative to the needle holding portion 28 in the circumferential direction (leftward).

After moving in the distal direction within the distal direction passage 190, the pair of projections 52, the projections 52 reach the distal direction passage narrow portion 190a as illustrated in FIGS. 10C and 10D. In the distal direction passage narrow portion 190a, the projection 52 comes in contact with the edge portion 171 of the extending elastic portion 172 and passes through while elastically deforming the extending elastic portion 172 in a direction opposite to the direction into the distal direction passage 190. As illustrated in FIGS. 11A and 11B, the extending elastic portion 172 elastically returns to its original posture after the passage of the projection 52, causing vibration to function as a click feeling generator that generates a click feeling at this time. That is, the passage of the projection 52 is transmitted to the audio sense of the user by sound, or transmitted as vibration to the tactile sense of the user grasping the medical instrument assembly 110 due to vibration via the device.

With the pair of projections 52 moved to the first and second puncture positions 177 and 188a, the needle 16 is sufficiently exposed from the distal end opening 58a of the outer cylinder 140. When the patient is punctured with the needle 16, the user presses the plunger 22 to administer the medicinal solution. In this state, the guide projecting portion 173 of the extending elastic portion 172 is located close to the proximal side of the projection 52, with the distal end inclined edge portion 173c of the guide projecting portion 173 facing the projection 52. Therefore, when the syringe 12 retracts from the distal side, the proximal end inclined side 52c of the pair of projections 52 comes into contact with the distal end inclined edge portion 173c of the guide projecting portion 173 as illustrated in FIGS. 11C and 11D, thereby generating a resistance force to reduce the retraction force of the inner cylinder 36. With this configuration, even with a slight retraction of the medical instrument assembly 110 by the user at the time of puncture with the needle 16 or administration of the medicinal solution, it is possible to suppress disengagement of the needle 16 from the patient, leading to satisfactory administration of the medicinal solution by the user.

After administration of the medicinal solution, the medical instrument assembly 110 is separated from the patient, thereby allowing the outer cylinder 140 and the cover 42 to be biased by the spring 38 to move relative to the inner cylinder 36 in the distal direction. Accordingly, the projection 52 elastically deforms the guide projecting portion 173 of the extending elastic portion 172 in the direction opposite to the direction into the proximal direction passage 192 in the proximal direction passage narrow portion 192a. Thereafter, the projection 52 moves within the proximal direction passage 192 in the proximal direction. At this time, mutual contact between the proximal end inclined side 52c and the distal end inclined edge portion 173c restricts the projection 52 from returning to the distal direction passage 190.

With aggressive movement in the proximal direction, the projection 52 also easily passes through the proximal direction passage narrow portion 178b formed by the side elastic portion 174, and moves to the first and the second final position 178a and 186a, as illustrated in FIGS. 12A and 12B. At the first and second final positions 178a and 186a, the lock projecting portion 174c of the side elastic portion 174 narrows the proximal direction passage 192. As also illustrated in FIGS. 12C and 12D, the inclined portion of the lock projecting portion 174c and the edge portion 156a of the peripheral wall 156 of the second guide path 180 guide the projection 52 in a direction away from the proximal direction passage 192. This configuration restricts the disengagement of the projection 52 from the first and second final positions 178a and 186a, that is, the re-advancement of the inner cylinder 36 and the syringe 12 to the outer cylinder 140.

As described above, same effects as those of the first embodiment can be obtained also with the protective device 114 and the medical instrument assembly 110 according to the second embodiment. In other words, the protective device 114 includes the guide projecting portion 173 of the extending elastic portion 172 that generates a resistance force against the relative movement of the inner cylinder 36 in the proximal direction with respect to the outer cylinder 140 by the biasing force of the spring 38 at the first puncture position 177 or in the vicinity thereof. With this configuration, it is possible to reduce the retraction force of the inner cylinder 36 with respect to the outer cylinder 140 due to the biasing force of the spring 38 in the exposed state of the needle 16. For example, the retraction force of the inner cylinder 36 with respect to the outer cylinder 140 is suppressed by the resistance force even when a force of a user pressing the syringe 12 onto the patient as the puncture target is decreased with the pushing operation of the plunger 22 at the time of administration of the medicinal solution, making it possible to suppress inadvertent retraction of the inner cylinder 36 with respect to the outer cylinder 140. Furthermore, because the first guide path 170 and the second guide path 180 are formed in different shapes from each other, the protective device 114 can change the action to be applied to the pair of projections 52, leading to further free designing of the resistance force to be generated in the inner cylinder 36. Furthermore, the position where click feeling is generated can be designed more freely.

Third Embodiment

Figure 13A:
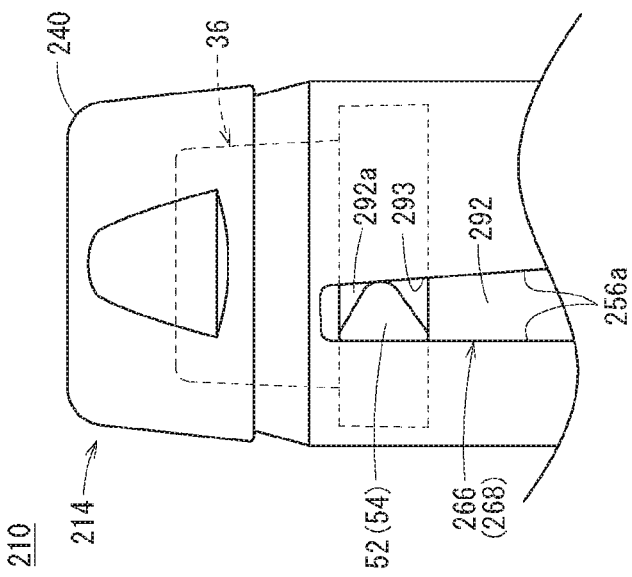
FIG. 13A is a first side view illustrating a distal end portion of a medical instrument assembly to which a protective device according to a third embodiment is attached.
Figure 13B:
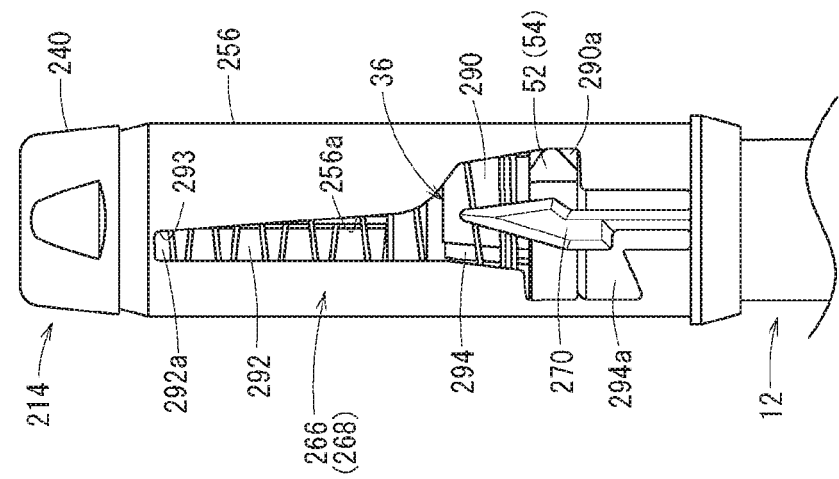
FIG. 13B is a second side view illustrating an opposite side of the first side view of FIG. 13A.

Next, a medical instrument assembly 210 and a protective device 214 according to a third embodiment will be described with reference to FIGS. 13A and 13B. The protective device 214 of the medical instrument assembly 210 according to the third embodiment has a guide path structure 268 in an outer cylinder 240, different from the guide path structures 68 and 168 according to the first and second embodiments.

The guide path structure 268 is configured with a pair of guide paths 266 formed in the same shape at a position shifted by 180° in the circumferential direction of the outer cylinder 240. Similarly to the guide path 66 of the first embodiment, this guide path 266 includes an initial position 290a, an initial passage 290, an intermediate passage 292, a puncture position 292a, a late passage 294, and a final position 294a, and also includes a proximal side elastic piece 270.

Note that the guide path 266 includes the intermediate passage 292 formed by an edge portion 256a of a peripheral wall 256 without including the distal side elastic piece 80, with the intermediate passage 292 gradually narrowing in the distal direction. A width of the distal side (puncture position 292a) of the intermediate passage 292 is set to be slightly narrower than the width of the projection 52 and defined as a clamping portion 293. With this configuration, the edge portion 256a of the peripheral wall 256 of the intermediate passage 292 forming the clamping portion 293 clamps the projection 52 when the projection 52 moves to the puncture position 292a, so as to generate a weak frictional force (holding force) against the projection 52. The frictional force is smaller than the biasing force applied by the spring 38 to the inner cylinder 36, and is such a degree as to hold the projection 52 lightly. In other words, the guide path 266 uses the edge portion 256a of the peripheral wall 256 to constitute the clamping portion 293, which is a resistance force generator that generates a resistance force to the projection 52 that has moved to the puncture position 292a.

In this manner, the projection 52 (inner cylinder 36) is held lightly while being clamped by the edge portion 256a of the peripheral wall 256 at the puncture position 292a. Therefore, even when the force of the user pushing the syringe 12 toward the puncture target with the pushing operation of the plunger 22 decreases at the time of administration of the medicinal solution, it is possible to suppress retraction from the puncture position 292a by the frictional force. Moreover, when the medical instrument assembly 210 is separated from the patient after the puncture, the clamping of the projection 52 is released by the biasing force of the spring 38, leading to satisfactory movement of the projection 52 from the puncture position 292a to the final position 294a.

As described above, the protective device 214 and the medical instrument assembly 210 according to the third embodiment also have the same effects as those of the protective devices 14, 114 and the medical instrument assemblies 10, 110 according to the first and second embodiments. In addition, with a configuration in which the edge portion 256a of the guide path 266 forms the clamping portion 293 that clamps the cam structure 54 to generate the frictional force, it is possible to easily design the resistance force to be generated in the inner cylinder 36. Furthermore, because the shape of the guide path 266 is simplified, making it possible to obtain higher efficiency in the manufacturing of the protective device 214.

Note that the shape and position of the edge portion 256a of the peripheral wall 256 for generating the resistance force at the projection 52 are not particularly limited and may take various shapes. For example, the width of the intermediate passage 292 in the vicinity of the proximal end of the puncture position 292a may be formed to be narrower than the projection 52 to form the clamping portion 293, and the resistance force may be generated in the projection 52 by the clamping portion 293. In this case, a weak frictional force is generated by the contact between the clamping portion 293 and the projection 52 immediately before the projection 52 reaches a puncture position 492a, and this frictional force is removed when the projection 52 moves to the puncture position 292a, making it possible to allow the user to sense that the projection 52 has moved to the puncture position 292a.

Fourth Embodiment

Figure 14:
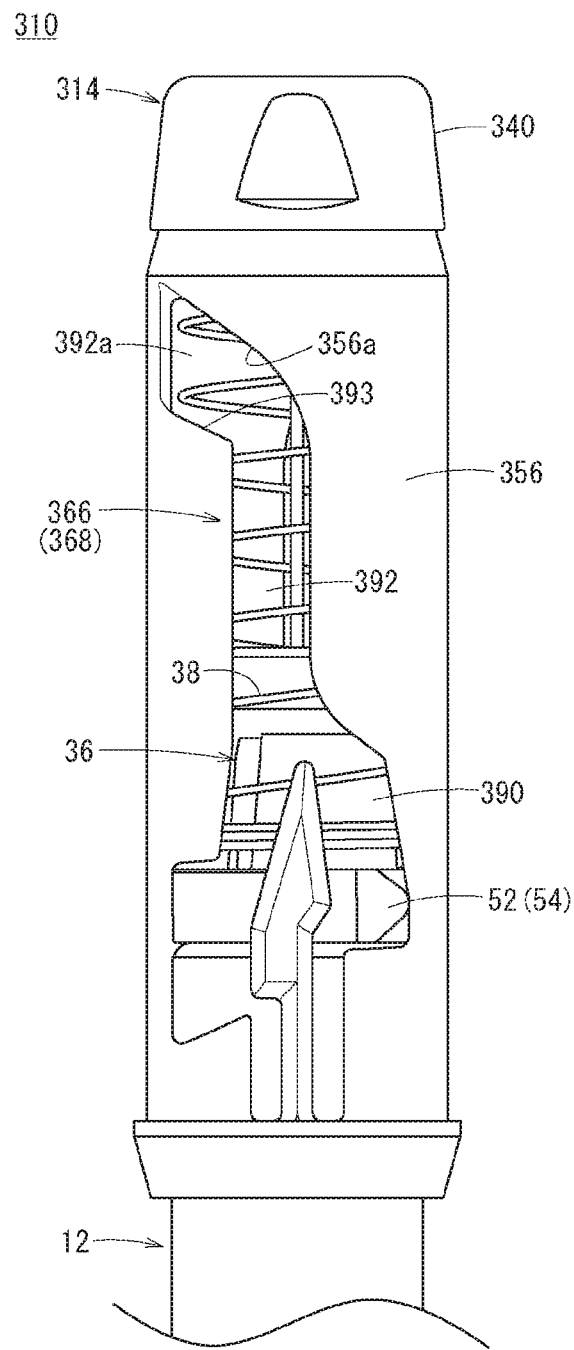
FIG. 14 is a partial side view illustrating a distal end portion of a medical instrument assembly to which a protective device according to a fourth embodiment is attached.

As illustrated in FIGS. 14, 15A, and 15B, a protective device 314 of a medical instrument assembly 310 according to a fourth embodiment are different from the guide path structures 68, 168, and 268 of the first to third embodiments in that a distal end portion of an intermediate passage 392 of a guide path 366 of a guide path structure 368 is inclined. That is, the distal end portion of the intermediate passage 392 of the guide path 366 includes an inclined edge portion 393 formed by cutting out an edge portion 356a of a peripheral wall 356 of the outer cylinder 340 diagonally (in the circumferential direction) in a direction of separating from an initial passage 390 in the distal direction and in the circumferential direction of the outer cylinder 140 and is inclined diagonally (in the circumferential direction) in the distal direction in the vicinity of the proximal end of a puncture position 392a. In this case, a gap between the edge portion 356a on the distal side of the peripheral wall 356 and the inclined edge portion 393 is set to such dimension to enable the projection 52 to be arranged, and the puncture position 392a is formed between the edge portion 356a on the distal side of the peripheral wall 356 and the inclined edge portion 393. Moreover, the edge portion 356a on the distal side of the peripheral wall 356 is also inclined with respect to the axial direction of the outer cylinder 340 similarly to the inclined edge portion 393.

The inclination angle of the inclined edge portion 393 is preferably set to an appropriate angle in accordance with the biasing force of the spring 38 or the like. For example, an inclination angle $\theta$ of the inclined edge portion 393 illustrated in FIG. 15B is preferably set in a range of 45° to 85° with respect to the axial direction of the outer cylinder 340, more preferably in a range of 50° to 80°, still more preferably in a range of 60° to 70°. In the fourth embodiment, the inclination angle $\theta$ is set to 65°. With the inclination angle $\theta$ smaller than 45°, the projections 52 are liable to move and there is a possibility that sufficient resistance force might not be generated. On the other hand, when the inclination angle $\theta$ is larger than 85°, the inclined edge portion 393 might restrict the retraction of the projection 52 after the puncture, and might suppress movement of the cam structure 54 from the puncture position 392a to the final position, leading to a failure in accommodating the needle tip 16a of the needle 16 in the outer cylinder 340.

When puncturing with the needle 16, the projection 52 passes through the proximal end portion of the intermediate passage 392 extending linearly, and rotates along the edge portion 356a on the distal side of the peripheral wall 356 inclined with respect to the axial direction of the outer cylinder 340 so as to move inside the distal end portion of the intermediate passage 392 to reach the puncture position 392a. When the projection 52 moves from the puncture position 392a in the proximal direction, the projection 52 comes in contact with the inclined edge portion 393 located in the vicinity of the proximal end of the puncture position 392a. That is, the guide path 366 uses the edge portion 356a of the peripheral wall 356 in the vicinity of the proximal end of the puncture position 392a to constitute the inclined edge portion 393, which is a resistance force generator that generates a resistance force to the projection 52. After the puncture, the projection 52 moves along the inclined edge portion 393 by the biasing force of the spring 38, and can be satisfactorily removed from the puncture position 392a.

In this manner, the protective device 314 includes, in the vicinity of the proximal end of the puncture position 392a, the inclined edge portion 393 inclined at a predetermined angle with respect to the axial direction of the outer cylinder 340 and constituting a portion of the guide path 366, and can constitute the resistance force generator from the inclined edge portion 393. Note that the shape of the inclined edge portion 393 is not limited to the above shape. For example, the inclined edge portion 393 may be inclined diagonally toward the initial passage 390 side in the distal direction and in the circumferential direction of the outer cylinder 140.

Fifth Embodiment

As illustrated in FIGS. 16A and 16B, a protective device 414 of a medical instrument assembly 410 according to a fifth embodiment is configured such that an inner surface 441 constituting a hollow portion 440a of an outer cylinder 440 is formed in a small diameter at the puncture position 492a or in the vicinity of the puncture position 492a, differing from the outer cylinders 40, 140, 240, and 340 according to the first to fourth embodiments. More specifically, the inner surface 441 of the outer cylinder 440 is gradually reduced in diameter in the distal direction, and is to be a contact inner surface 441a slightly smaller in diameter than the outer diameter of the annular portion 46 of the inner cylinder 36 at the puncture position 492a of a guide path 466 (guide path structure 468). With this configuration, when the inner cylinder 36 moves to the distal side of the outer cylinder 340 at the time of puncture of the needle 16, the contact inner surface 441a of the outer cylinder 440 comes in contact with the inner cylinder 36 and a weak frictional force can be generated. The frictional force is set to be smaller than the biasing force to be applied by the spring 38 to the inner cylinder 36, and is set to such a degree that the outer cylinder 440 holds the inner cylinder 36 lightly. In other words, the contact inner surface 441a of the outer cylinder 440 functions as a resistance force generator that generates a resistance force on the inner cylinder 36. Therefore, the guide path structure 468 that guides the projection 52 can be freely designed.

In this manner, even with the contact inner surface 441a of the outer cylinder 440 to constitute the resistance force generator, it is possible to obtain the same effects as those of the protective devices 14, 114, 214, and 314 according to the first to fourth embodiments. Therefore, even when the force of the user pushing the syringe 12 toward the puncture target with the pushing operation of the plunger 22 decreases at the time of administration of the medicinal solution, the outer cylinder 440 holds the inner cylinder 36 to generate the resistance force, thereby suppressing retraction of the inner cylinder 36 with respect to the outer cylinder 440. After puncturing, the inner cylinder 36 can be removed from the hold of the outer cylinder 440 by the biasing force of the spring 38, leading to satisfactory retraction of the inner cylinder 36.

Note that the position of the contact inner surface 441a of the outer cylinder 440 may be proximal of the puncture position 492a. In this case, a weak frictional force is generated by the contact between the contact inner surface 441a and the inner cylinder 36 immediately before the projection 52 reaches the puncture position 492a, and this frictional force is removed when the projection 52 moves to the puncture position 492a, making it possible to allow the user to sense that the projection 52 has moved to the puncture position 492a. Furthermore, the contact inner surface 441a functioning as a resistance force generator can be achieved not only by forming the inner surface 441 of the outer cylinder 440 with a small diameter, but also by providing one or more projecting portions (not illustrated) protruding inward in the radial direction from the inner surface 441. Furthermore, the resistance force generator may be formed as a contact inner surface that not only generates a resistance force by coming into contact with the annular portion 46 but also generates, for example, a frictional force (resistance force) by forming a thick inner side of the distal end portion of the outer cylinder 440 and by allowing the inner surface 441 to come in contact with the protruding wall portion 48 of the inner cylinder 36.

The present invention is not limited to the above-described embodiment, and various modifications are possible of course without departing from the scope and spirit of the present invention. As an example, the medical instrument assembly 10 and the protective device 14 may combine two or more resistance force generators according to the first to fifth embodiments. For example, it is allowable to have a configuration in which a resistance force is generated in the projection 52 by the distal side elastic piece 80 (elastically deformable portion) according to the first embodiment, with the inner face (contact inner surface 441a) of the outer cylinder 40 coming in contact with the inner cylinder 36 to generate a resistance force.

Furthermore, embodiments of the present invention can be applied not only to the syringe 12 (prefilled syringe) described above as a medical instrument but also to various medical instruments. Example of other medical instruments include a puncture tool for blood collection and an injection needle to be attached to a syringe.

What is claimed is:

1. A protective device configured to be attached to a medical instrument that comprises a needle including a needle tip at distal end thereof, and a needle holding portion for holding the needle, the protective device being configured to cover the needle tip after puncturing a puncture target with the needle, the protective device comprising:

an inner member configured to rotate in a circumferential direction relative to the medical instrument and comprising a cam structure, the cam structure comprising a projection protruding outward in a radial direction; and an outer cylinder configured to cover at least a portion of the needle and an outside of the inner member before puncture; and a biasing member configured to bias the outer cylinder in a distal direction relative to the inner member;

wherein the outer cylinder comprises a guide path structure, the guide path structure comprising one or more guide paths that receive the cam structure, the guide path structure being configured to rotate the inner member in accordance with relative movement of the outer cylinder;

wherein the outer cylinder is configured to move in a proximal direction relative to the inner member at a time of puncture to expose the needle tip and to move in the distal direction relative to the inner member by a biasing force of the biasing member after puncture to cover the needle tip;

wherein the guide path structure comprises:

a distal direction passage configured to guide the cam structure from (i) an initial position at which the cam structure is disposed before puncture, to (ii) a puncture position to which the cam structure moves at the time of puncture, the puncture position being distal of the initial position and rotationally offset in the circumferential direction from the initial position, a proximal direction passage configured to guide the cam structure from (i) the puncture position, to (ii) a final position to which the cam structure moves after puncture, the final position being proximal of the puncture position, and a proximal direction passage elastically deformable portion that, together with an edge portion of the proximal direction passage, defines a proximal direction passage narrow portion in a middle of the proximal direction passage, the proximal direction passage narrow portion having a width smaller than a width of the projection;

wherein the distal direction passage comprises an inclined passage extending diagonally in the distal direction;

wherein the proximal direction passage extends linearly along an axial direction of the outer cylinder at least from a vicinity of a proximal end of the puncture position to the proximal direction passage elastically deformable portion;

wherein the proximal direction passage elastically deformable portion is configured to elastically deform so as to widen the proximal direction passage narrow portion in accordance with contact by the projection, such that the cam structure is allowed to move from the puncture position to the final position, and such that the cam structure is restricted from moving from the final position to the proximal direction passage by contact with the projection;

wherein the outer cylinder comprises a resistance force generator configured to generate a resistance force against relative movement of the inner member in the proximal direction relative to the outer cylinder when the cam structure is in the puncture position or in a vicinity of the puncture position; and wherein the resistance force is smaller than the biasing force of the biasing member when the cam structure is in the puncture position.

2. The protective device according to claim 1,
wherein the guide path structure comprises the resistance force generator; and
the resistance force generator is configured to come in contact with a side portion or a proximal end portion of the cam structure when the cam structure is in the puncture position or in the vicinity of the puncture position.

3. The protective device according to claim 2,
wherein the guide path structure comprises, in a vicinity of a proximal end of the puncture position, an inclined edge portion that is inclined at a predetermined angle relative to the axial direction of the outer cylinder; and
the resistance force generator comprises the inclined edge portion, the inclined edge portion being configured to generate the resistance force by contacting with the projection when the cam structure is in the puncture position or in the vicinity of the puncture position.

4. The protective device according to claim 1,
wherein the outer cylinder includes a contact inner surface configured to contact an outer surface of the inner member; and
wherein the resistance force generator comprises the contact inner surface, the contact inner surface being configured to generate the resistance force by contacting the outer surface of the inner member when the cam structure is in the puncture position or in the vicinity of the puncture position.

5. A medical instrument assembly comprising:
the protective device according to claim 1; and
the medical instrument to which the protective device is attached.

6. The medical instrument assembly according to claim 5,
wherein the medical instrument is a prefilled syringe that comprises a barrel portion formed on a proximal side of the needle holding portion, a liquid stored in the barrel portion, and a cap for sealing the needle tip, and the prefilled syringe being configured to discharge the liquid from the needle tip.

7. A protective device configured to be attached to a medical instrument that comprises a needle including a needle tip at distal end thereof, and a needle holding portion for holding the needle, the protective device being configured to cover the needle tip after puncturing a puncture target with the needle, the protective device comprising:
an inner member configured to rotate in a circumferential direction relative to the medical instrument and comprising a cam structure, the cam structure comprising a projection protruding outward in a radial direction; and
an outer cylinder configured to cover at least a portion of the needle and an outside of the inner member before puncture; and
a biasing member configured to bias the outer cylinder in a distal direction relative to the inner member;
wherein the outer cylinder comprises a guide path structure, the guide path structure comprising one or more guide paths that receive the cam structure, the guide path structure being configured to rotate the inner member in accordance with relative movement of the outer cylinder;
wherein the outer cylinder is configured to move in a proximal direction relative to the inner member at a time of puncture to expose the needle tip and to move in the distal direction relative to the inner member by a biasing force of the biasing member after puncture to cover the needle tip;
wherein the guide path structure comprises:
a distal direction passage configured to guide the cam structure from (i) an initial position at which the cam structure is disposed before puncture, to (ii) a puncture position to which the cam structure moves at the time of puncture, the puncture position being distal of the initial position and rotationally offset in the circumferential direction from the initial position, and
a proximal direction passage configured to guide the cam structure from (i) the puncture position, to (ii) a final position to which the cam structure moves after puncture, the final position being proximal of the puncture position;
wherein the guide path structure comprises an elastically deformable portion that comprises:
an elastically deformable main body connected to a peripheral wall of the outer cylinder, and
a protruding portion protruding from the elastically deformable main body into the guide path structure; and
wherein the protruding portion is configured to generate a resistance force against relative movement of the inner member in the proximal direction relative to the outer cylinder when the cam structure is in the puncture position or in a vicinity of the puncture position by contact with the projection;
wherein the protruding portion is configured to come in contact with a side portion or a proximal end portion of the cam structure when the cam structure is in the puncture position or in the vicinity of the puncture position; and
wherein the resistance force is smaller than the biasing force of the biasing member when the cam structure is in the puncture position.

8. The protective device according to claim 7,
wherein the protruding portion comprises, on a distal side thereof, a distal side inclined surface having a protruding amount into the guide path structure that gradually increases in the proximal direction.

9. The protective device according to claim 7,
wherein the elastically deformable main body comprises:
a distal end portion connected to a peripheral wall of the outer cylinder, and
a proximal end portion that is a free end;
wherein the elastically deformable main body extends from a distal end of the guide path structure in the proximal direction along the axial direction of the outer cylinder to a location past the puncture position; and wherein the protruding portion is disposed at the proximal end portion.

10. The protective device according to claim 7,
wherein the elastically deformable main body comprises:
a proximal end portion connected to a peripheral wall of the outer cylinder, and
a distal end portion that is a free end,
wherein the elastically deformable main body extends from a proximal end of the guide path structure or from a middle of the distal direction passage in the distal direction along the axial direction of the outer cylinder to the vicinity of a proximal end of the puncture position; and
wherein the protruding portion is disposed at the distal end portion.

11. The protective device according to claim 10,
wherein the elastically deformable portion is disposed between the initial position and the puncture position in the circumferential direction of the outer cylinder, and is configured to restrict movement of the cam structure from the puncture position to the initial position.

12. A medical instrument assembly comprising:
the protective device according to claim 7; and
the medical device instrument to which the protective device is attached.

13. The medical instrument assembly according to claim 12,
wherein the medical instrument is a prefilled syringe that comprises a barrel portion formed on a proximal side of the needle holding portion, a liquid stored in the barrel portion, and a cap for sealing the needle tip, and the prefilled syringe being configured to discharge the liquid from the needle tip.

14. A protective device configured to be attached to a medical instrument that comprises a needle including a needle tip at distal end thereof, and a needle holding portion for holding the needle, the protective device being configured to cover the needle tip after puncturing a puncture target with the needle, the protective device comprising:
an inner member configured to rotate in a circumferential direction relative to the medical instrument and comprising a cam structure, the cam structure comprising a projection protruding outward in a radial direction; and
an outer cylinder configured to cover at least a portion of the needle and an outside of the inner member before puncture; and
a biasing member configured to bias the outer cylinder in a distal direction relative to the inner member;
wherein the outer cylinder comprises a guide path structure, the guide path structure comprising one or more guide paths that receive the cam structure, the guide path structure being configured to rotate the inner member in accordance with relative movement of the outer cylinder;
wherein the outer cylinder is configured to move in a proximal direction relative to the inner member at a time of puncture to expose the needle tip and to move in the distal direction relative to the inner member by a biasing force of the biasing member after puncture to cover the needle tip;
wherein the guide path structure comprises:
a distal direction passage configured to guide the cam structure from (i) an initial position at which the cam structure is disposed before puncture, to (ii) a puncture position to which the cam structure moves at the time of puncture, the puncture position being distal of the initial position and rotationally offset in the circumferential direction from the initial position, and
a proximal direction passage configured to guide the cam structure from (i) the puncture position, to (ii) a final position to which the cam structure moves after puncture, the final position being proximal of the puncture position;
wherein the guide path structure comprises a clamping portion, the clamping portion having a width narrower than a width of the projection at the puncture position or in the vicinity of a proximal end of the puncture position;
wherein an edge portion that defines the clamping portion is configured to generate a resistance force against relative movement of the inner member in the proximal direction relative to the outer cylinder when the cam structure is in the puncture position or in a vicinity of the puncture position by clamping the projection;
wherein the edge portion is configured to come in contact with a side portion or a proximal end portion of the cam structure when the cam structure is in the puncture position or in the vicinity of the puncture position; and
wherein the resistance force is smaller than the biasing force of the biasing member when the cam structure is in the puncture position.

15. A medical instrument assembly comprising:
the protective device according to claim 14; and
the medical instrument to which the protective device is attached.

16. The medical instrument assembly according to claim 15,
wherein the medical instrument is a prefilled syringe that comprises a barrel portion formed on a proximal side of the needle holding portion, a liquid stored in the barrel portion, and a cap for sealing the needle tip, and the prefilled syringe being configured to discharge the liquid from the needle tip.

17. A protective device configured to be attached to a medical instrument that comprises a needle including a needle tip at distal end thereof, and a needle holding portion for holding the needle, the protective device being configured to cover the needle tip after puncturing a puncture target with the needle, the protective device comprising:
an inner member configured to rotate in a circumferential direction relative to the medical instrument and comprising a cam structure, the cam structure comprising a projection protruding outward in a radial direction;
an outer cylinder configured to cover at least a portion of the needle and an outside of the inner member before puncture; and
a biasing member configured to bias the outer cylinder in a distal direction relative to the inner member;
wherein the outer cylinder comprises a guide path structure, the guide path structure comprising one or more guide paths that receive the cam structure, the guide path structure being configured to rotate the inner member in accordance with a relative movement of the outer cylinder,
wherein the outer cylinder is configured to move in a proximal direction relative to the inner member at a time of puncture to expose the needle tip and to move in the distal direction relative to the inner member by a biasing force of the biasing member after puncture to cover the needle tip;
wherein the guide path structure comprises:

a distal direction passage configured to guide the cam structure from (i) an initial position at which the cam structure is disposed before puncture, to (ii) a puncture position to which the cam structure moves at the time of puncture, the puncture position being distal of the initial position and rotationally offset in the circumferential direction from the initial position, and a proximal direction passage configured to guide the cam structure from (i) the puncture position, to (ii) a final position to which the cam structure moves after puncture, the final position being proximal of the puncture position;

wherein the distal direction passage comprises, in a vicinity of a proximal end of the puncture position, a click feeling generator configured to generate a click feeling upon passage of the cam structure;

wherein the click feeling generator is disposed at a position rotationally offset in the circumferential direction from the initial position; and wherein the click feeling generator comprises an elastically deformable portion configured to elastically deform by contact with the cam structure and is configured to generate the click feeling by elastic return of the elastically deformable portion after passage of the cam structure.

18. The protective device according to claim 17, wherein the elastically deformable portion comprises:
an elastically deformable main body connected to a peripheral wall of the outer cylinder, and a protruding portion protruding from the elastically deformable main body into the guide path structure; and wherein the elastically deformable main body is configured to elastically deform in the circumferential direction of the outer cylinder in accordance with contact between the protruding portion and the cam structure.

19. The protective device according to claim 18, wherein the protruding portion comprises a proximal side inclined surface having a protruding amount into the guide path structure that gradually increases in the distal direction.

20. The protective device according to claim 17, wherein a cover to cover the guide path structure is disposed on an outer circumferential surface of the outer cylinder.

21. A medical instrument assembly comprising:
the protective device according to claim 17; and
the medical instrument to which the protective device is attached.

22. The medical instrument assembly according to claim 21,
wherein the medical instrument is a prefilled syringe that comprises a barrel portion formed on a proximal side of the needle holding portion, a liquid stored in the barrel portion, and a cap for sealing the needle tip, and the prefilled syringe being configured to discharge the liquid from the needle tip.

* * * * *